United States Patent [19]
Jeannotte et al.

[11] Patent Number: 5,402,241
[45] Date of Patent: Mar. 28, 1995

[54] OPTICAL PROBE FOR FLUID LIGHT TRANSMISSION PROPERTIES

[75] Inventors: Anthony C. Jeannotte, Foxboro, Mass.; Arthur Colvin, Gaithersburg, Md.

[73] Assignee: The Foxboro Company, Foxborough, Mass.

[21] Appl. No.: 775,872

[22] Filed: Oct. 15, 1991

Related U.S. Application Data

[63] Continuation-in-part of Ser. No. 514,061, Apr. 24, 1990, Pat. No. 5,181,082, which is a continuation-in-part of Ser. No. 330,533, Mar. 30, 1989, Pat. No. 5,007,740.

[51] Int. Cl.⁶ .................. G01N 21/00; G01N 1/10
[52] U.S. Cl. .................. 356/436; 356/440; 356/246; 250/576
[58] Field of Search .................. 356/435–442, 356/432–434, 244, 246, 336, 338; 250/573–576, 227.11, 227.25

[56] References Cited

U.S. PATENT DOCUMENTS

| | | |
|---|---|---|
| Re. 30,391 | 9/1980 | Liston . |
| 2,203,720 | 6/1940 | Dale . |
| 3,141,094 | 7/1964 | Strickler ............... 356/440 |
| 3,431,424 | 3/1969 | Allen . |
| 3,723,062 | 3/1973 | Dahms . |
| 3,734,621 | 5/1973 | Moody et al. . |
| 3,740,155 | 6/1973 | Keller et al. ............... 356/246 |
| 3,746,452 | 7/1973 | Teboul et al. . |
| 3,869,215 | 3/1975 | Nolan ............... 356/246 |
| 4,040,743 | 8/1977 | Villaume et al. . |
| 4,152,070 | 5/1979 | Kushner et al. . |
| 4,171,909 | 10/1979 | Kramer et al. . |
| 4,320,978 | 3/1982 | Sato . |
| 4,477,186 | 10/1984 | Carlson . |
| 4,561,779 | 12/1985 | Nagamune et al. . |
| 4,591,268 | 5/1986 | Lew . |
| 4,682,895 | 7/1987 | Costello ............... 250/227.11 |
| 4,707,134 | 11/1987 | Mclochlan et al. ............... 356/342 |
| 4,730,882 | 3/1988 | Messerschmidt . |
| 4,753,530 | 6/1988 | Knight et al. ............... 356/435 |
| 4,851,665 | 7/1989 | Peravento et al. ............... 356/436 |
| 5,007,740 | 4/1991 | Jeannotte et al. . |
| 5,046,854 | 9/1991 | Weller et al. ............... 356/246 |

FOREIGN PATENT DOCUMENTS

| | | |
|---|---|---|
| 2534763 | 3/1976 | Germany . |
| 3609156 | 9/1987 | Germany . |
| 2194333 | 3/1988 | United Kingdom . |
| WO88/02109 | 3/1988 | WIPO . |
| WO90/12309 | 10/1990 | WIPO . |

OTHER PUBLICATIONS

M. Rioux, et al., "Linear, annular, and radial focusing with axicons and applications to laser machining", *Applied Optics*, 17(10), 15 May 1978, pp. 1532–1536.

"Nouvelle Optode Passive Pour la Spectrofluoroimetrie et la Spectrometrie Raman", 17–19 May, 1988; Opto 88; pp. 294–299.

G. Boisde, et al., "Aspects of Optical Fibers and Spectrophotometric Sensors in Chemical Process and Industrial Environments", *ECO1*, 22–23 Sep. 1988, Hamburg, GFR, SPIE vol. 1012, 'In-Process Measurements', 1988, pp. 58–65.

*Primary Examiner*—Hoa Q. Pham
*Attorney, Agent, or Firm*—Wigman, Cohen, Leitner & Myers

[57] ABSTRACT

Radiant energy is transmitted to a probe element including an interior conical reflecting surface and a fluid sample chamber. Portions of the light which have been transmitted, partially attenuated, or scattered by a fluid sample in the sample chamber are directed by at least a portion of the interior conical reflecting surface to means for collecting the transmitted, partially attenuated, or scattered light. A stilling valve incorporated into the probe element enables elimination of entrained gas bubbles from the chamber.

40 Claims, 10 Drawing Sheets

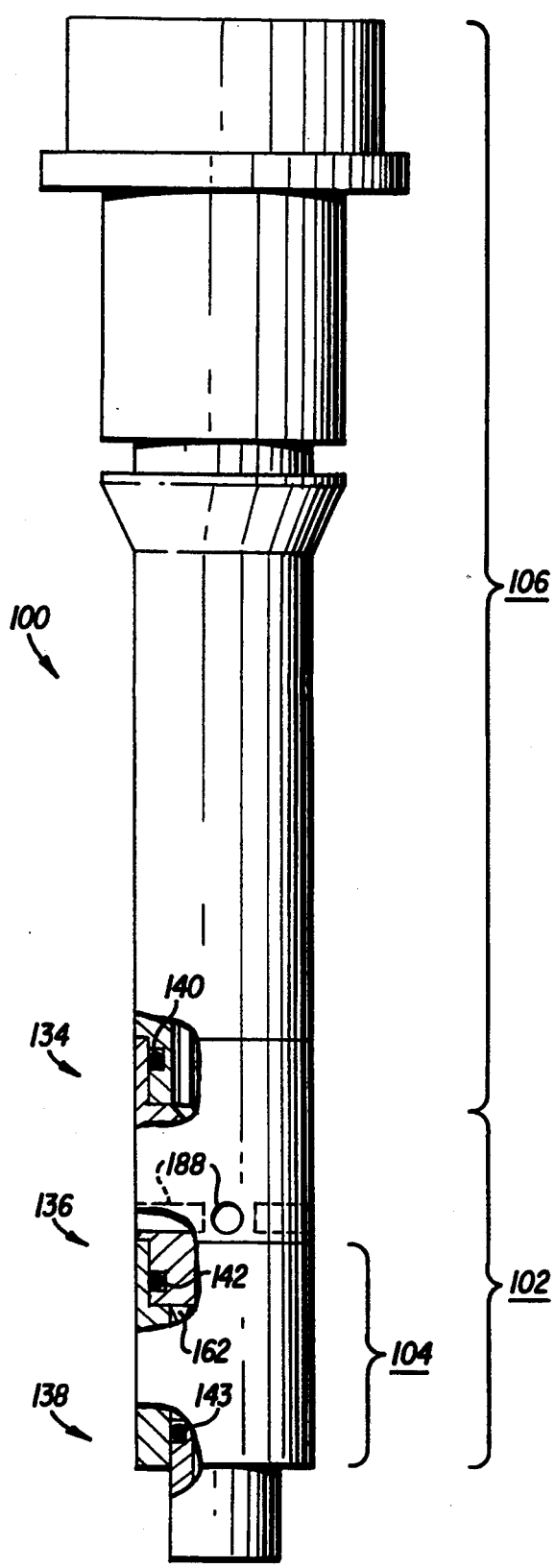
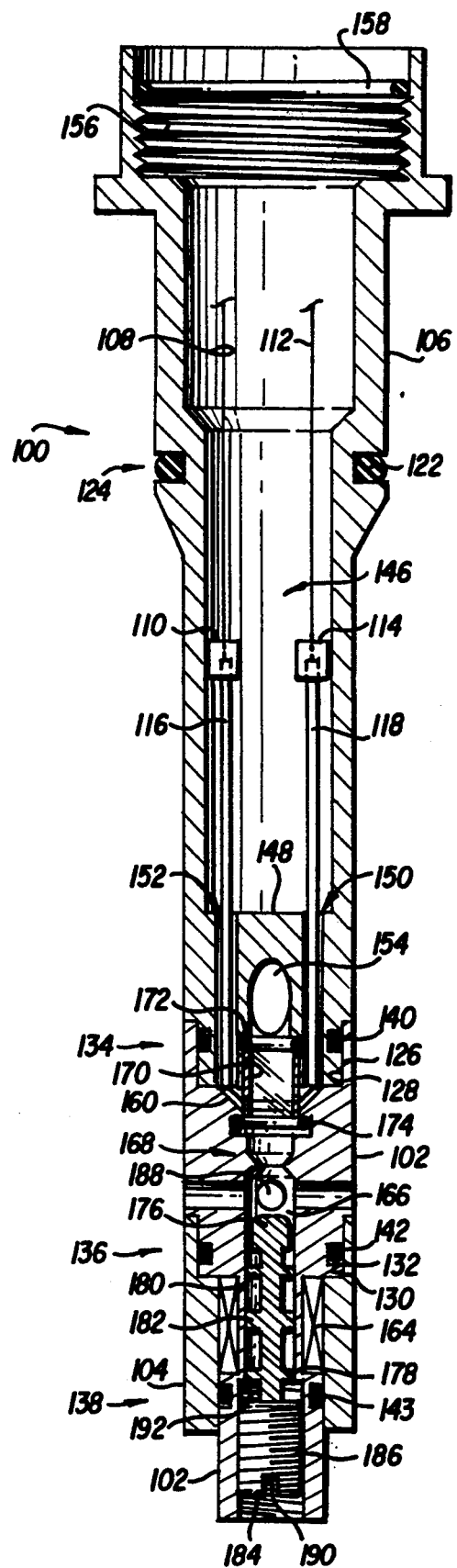
FIG. 16
FIG. 17

OPTICAL PROBE FOR FLUID LIGHT TRANSMISSION PROPERTIES

RELATION TO OTHER APPLICATIONS

This application is a continuation-in-part of application Ser. No. 07/514,061, filed 24 Apr., 1990, now U.S. Pat. No. 5,181,082, which is a continuation-in-part of application Ser. No. 07/330,533, filed 30 Mar. 1989, now U.S. Pat. No. 5,007,740.

TECHNICAL FIELD

This invention relates to optical probes for sensing fluid characteristics optically, and particularly to optical analysis of a fluid sample in a sample chamber. More particularly, the present invention is directed to a combination optical probe and stilling well for optical sampling of a fluid admitted to a sample chamber. Improvements to this class of the probe include increasing the manufacturability, reliability, efficiency, and reduce the cost of this class of probe. Additional features include increased sensitivity, providing a wider practical range of sample materials and wavelengths of operation. The need for probe-mounted electronics is also eliminated, thus vastly increasing the ease with which the probe may be cleaned and sterilized. Additional improvements facilitate such cleaning and sterilization, and improve maintainability of the probe.

BACKGROUND OF THE INVENTION

As the advantages of fiber optic based communication and control of industrial processes becomes better known, increasing emphasis is being placed on various methods of simple, inexpensive, and reliable communication of optically sensed physical parameters, or measurands. Optical analysis of certain fluid materials offers known improvements over other techniques.

The measurement of the light transmitting or light scattering properties of a fluid ordinarily requires that a beam of light or radiant energy be passed through the fluid and subsequently directed towards a radiant energy detector. Optical apparatus for accomplishing this task have been used in which discrete components such as lenses, mirrors, or internally reflecting light guides are employed for the sampling apparatus. Optical fibers may be used to convey the light to the sensing apparatus and back to detection equipment. Examples of such techniques are illustrated in U.S. Pat. Nos. 4,591,268 to Lew ('268); 4,320,978 to Sato ('978); and 4,152,070 to Kushner et al ('070). These methods are generally unsuited for direct submersion within the test fluid because the optical surfaces are derogated by fluid contact, i.e., dirt erosion, pitting, and dissolving of the surfaces.

The use of fiber optic light guides is recognized for permitting the measurement of the light transmitting or scattering properties of fluids in harsh environments, such as a process container or pipeline containing the fluid of interest. Thus, U.S. Pat. Nos. 4,040,743 to Villaume et al ('743) and 4,561,779 to Nagamune et al ('779) depict apparatus for the in-situ measurement of fluid suspensions. A similar approach described by H. Raab in *Technisches Messen*, 50, 1983(12), p. 475, is employed for the in-situ assay of certain fluids. A common feature of these known methods is the use of relatively small prisms having planar surfaces which act to bend a light beam through 90 degrees. Such prisms can be expensive to fabricate and difficult to align.

Conical reflecting elements have been previously described in the literature (cf. M. Rioux, et al, *Applied Optics*, 17(10), 1978, p. 1532). Their use has been primarily as imaging devices for objects disposed along the conical reflecting element's axis of revolution. As will become evident from the subsequent disclosure, the method and apparatus of the invention described herein depart from these known configurations and permit utilization of the interior conical reflecting surface in an off-axis manner.

In addition, since the present invention has application in the fermentation arts, it is useful and often necessary to minimize bubbles in the measurement area. Known passive bubble reducing techniques are inadequate when applied to a fermentor environment. Typically intricate and narrow passageways designed to promote drainage of foamy samples are ineffective, and may be prone to blockage from the solution, which is typically cell-laden.

For this reason, the present invention comprehends the inclusion of a valved still well or stilling chamber from which the bubbles and foam are effectively drained prior to measurement. The combination probe thus incorporates a stilling well chamber, which may be either electrically or pneumatically valved, and a novel optical probe. Such a valved still well embodiment includes an 'open' position in which the solution is free to pass through the measurement chamber, and a 'closed' position in which the bubbles and/or foam in the solution are permitted to drain briefly before the measurement.

For the purposes of this limited description, "fiber optic" "optical fiber", "light guide", and "radiant energy pathway" refer to optical communication paths, generally optical fibers. As used herein, the terms "radiant energy" and "light" are used interchangeably to refer to electromagnetic radiation of wavelengths between $3 \times 10^{-7}$ and $10^{-9}$ meters, and specifically includes infrared, visible, and ultraviolet light. For simplicity, such electromagnetic radiation may be referred to as simply "light." These terms specifically include both coherent and non-coherent optical power. "Monochromatic" refers to radiant energy composed substantially of a single wavelength. "Collimated" light refers to radiant power having rays which are rendered substantially parallel to a certain line or direction.

SUMMARY OF THE INVENTION

It is an object of this invention to provide improved apparatus for the introduction and collection of radiant energy into, through, and from a sample chamber.

Another object of the invention is the incorporation of a stilling mechanism to rapidly and effectively eliminate bubbles and/or foam in a fluid sample at the time of the measurement.

Further objectives include provision of methods and apparatus which are both cost-effective and capable of withstanding harsh process conditions.

A further object of the present invention is that it is to be easily and inexpensively manufactured.

The probe of the present invention is directed to using an interior conical reflecting surface to direct radiant energy into and out of a sample chamber. The apparatus of the present invention can utilize the conical reflecting surface off-axis. The invention broadly includes opto-mechanical components which carry light from a radiant energy source to a sample chamber, direct this light into the chamber containing a test fluid sample, and collect and redirect light which has been transmitted, partially attenuated or scattered by the sample towards a radiant energy detector.

The probe uses optical methods and apparatus for simplified remote measurement of the light transmitting or light scattering properties of a fluid, especially when it is necessary to confine the fluid to its natural process vessel, a pipe, or where environmental factors such as excessive temperature preclude the possibility of siting light sources or detectors in the immediate vicinity of the fluid. The invention facilitates measurement of fluid properties over a broad range of applications, including but not limited to the determination of dissolved impurity levels in process fluids, the turbidity of fluids such as the undissolved solids content of fermentation systems or particle sizing. Other measurements include filter bed breakthrough, water quality, carbon dioxide in beverages, sugar in organics, water in gasoline, methanol in gasoline, sulfates and phosphates in water, and the like.

The method and apparatus of the present invention are broadly directed to opto-mechanical components which carry light from a radiant energy source to a sample chamber containing a test fluid of interest, direct this light into the sample chamber and collect and redirect the light which has been transmitted, partially attenuated, or scattered towards a radiant energy detector.

More particularly, the apparatus is a probe for optically sampling a fluid in a test or sample chamber, which apparatus includes a source of radiant energy, an interior conical reflecting surface segment surrounding part of a sample chamber, a first portion of which reflecting surface is used for directing radiant energy through the sample chamber, another portion of the conical reflecting surface is used for collecting radiant energy from said chamber, a first pathway for conveying radiant energy to the first portion of the conical reflecting surface, and a second pathway for conveying radiant energy away from said sample chamber, via another portion or other portions of the reflecting surface, to a detector.

A feature of the present apparatus is the use of an interior conical reflecting surface to direct radiant energy into and out of the sample chamber. The conical reflector segment permits rapid, economical assembly and alignment of the optical elements, and improves the efficiency with which the light is transferred into and from the sample chamber.

Measurement of fermentation characteristics and fluids containing bubbles or foam which would obscure the measurement is facilitated by incorporating stilling apparatus in the probe design to enable elimination of such bubbles and/or foam in order to enable accurate measurement of the desired solution characteristic. This aspect of the present invention therefore includes a sample chamber (which may be longitudinally oriented) having at least one upper vent port, one or more lower side drain ports, and valve means to close the lower side drain port or ports. The valve may be either pneumatically or electrically operated; electric operation is preferred.

Improvements in the stilling apparatus include improved reliability and maintainability, and enable relatively easy cleaning of the interior portions of the probe, as well as the valve plunger which is used to seal the chamber. Another advantage of the present improved probe is refelected in that the diameter thereof becomes genereally smaller towards the distal end thereof, faciliting entry of the probe into a gallery. The probe can readily be sized for entry through a conventional container aperture of about 25 centimeters.

BRIEF DESCRIPTION OF THE DRAWING FIGURES

Numerous other features and advantages of the invention disclosed herein will be apparent upon examination of the several drawing figures forming a part hereof. Solid line arrows may be used to indicate light rays. In all views, like reference characters indicate corresponding parts or elements:

FIG. 3 illustrates an optical probe assembly according to another aspect of the present invention;

FIG. 16 illustrates in cross-sectional view major portions of an optical probe according to an improved embodiment of this invention;

FIG. 17 illustrates in detail the main elements of the probe according to FIG. 16;

DETAILED DESCRIPTION OF THE PREFERRED EMBODIMENTS

Figure 1:
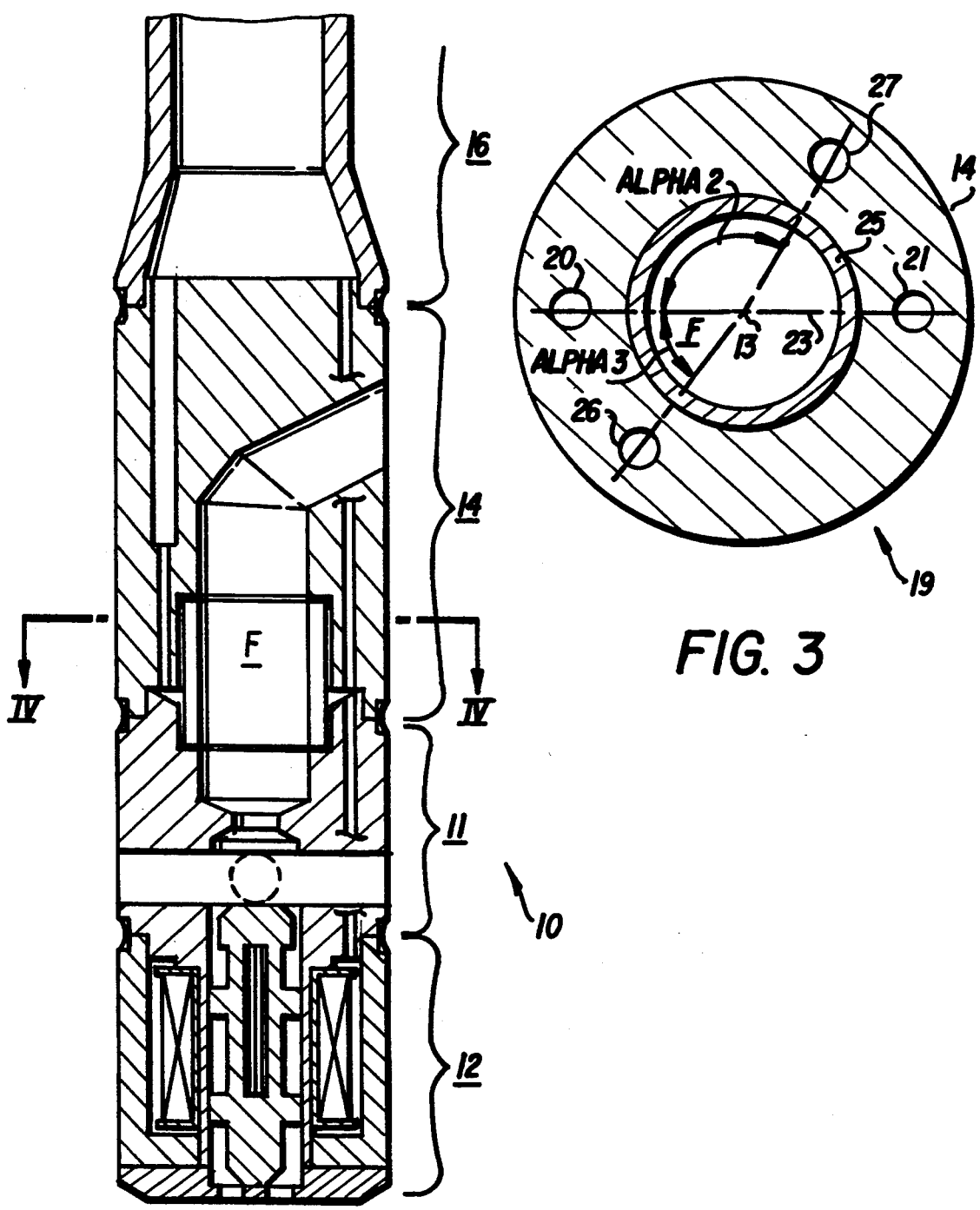
FIG. 1 illustrates in cross-sectional view major portions of an optical probe according to a primary aspect of this invention.

FIGS. 1 through 15 illustrate a preferred embodiment of the present probe invention. FIGS. 16 through 19 illustrate the improved probe according to another embodiment. Turning now to FIGS. 1, 4, 5, and 6 in which a probe 10 incorporating an interior conical reflector segment 11 is joined to a lower stilling valve actuator segment 12, to an upper main body segment 14 having an upper vent hole 15, and which in turn is joined to an extension tube segment 16. The probe 10 includes an axis of revolution 13 of the conical reflector segment 11 which, extended, may be the center line of the probe 10. The axis of revolution, of course, need not necessarily be the probe center line.

The interior conical reflector segment 11 is made by forming an interior conical reflecting surface 17 into the central area of a (preferably thick walled and hollow) cylindrical body. An interior conical reflecting surface 17 reflector segment 11 is easily fabricated by a simple cutting operation on a lathe. A quality reflecting surface 17 is obtained either by fine cutting of the reflecting surface 17 followed by a finish polish or by other well-known optical surface-finishing methods. A reflective overcoat (not shown) can be deposited to further improve the reflectivity of the reflecting surface 17. It will be appreciated by those skilled in the art that the light transmission and reflection properties of the optical elements described here will be influenced by the wavelength or wavelengths of light used to make the sample measurement, e.g., the light scattering or light transmitting properties of the sample fluid. Further, the probe 10 reflector and main body segments 11, 14 may be exposed to the process fluid (F) and therefore must be chosen so as to withstand the chemical and physical properties of their expected environment.

The probe 10 segments 11, 12, 14, 16 are essentially elongated and cylindrical in shape, though another shape may be used. The reflector segment 11 incorporates an interior conical reflecting surface 17; the segments 11, 14, 16 house the optical, electrical (or pneumatic) and mechanical components which carry light from a remotely located radiant energy source (not shown) to a sample chamber 18 containing a test fluid (F). Sample chamber 18 is formed in the central area joining the segments 11 and 14. A cylindrical, transparent section of glass, having a hollow, longitudinal central portion is used. The sample chamber 18 extends from above the juncture of the segments 11, 14 to a point below the conical reflecting surface 17 within the reflector segment 11. A probe 10 central passageway 38 extends above and below the sample chamber 18 in the segments 14, 11 respectively.

A plurality of longitudinal passages such as the light guide passages 28 provide access and protection for the light guides 20, 21, 26 entering through the segments 11, 14 and portions of the segments 12, 16. These passageways 28 additionally provide for precise alignment of the light guides 20, 21, 26 at the desired radial angle and radial distance from the centerline of the segment 14 corresponding to the axis of revolution 13 of the reflector segment 11. Wires (not shown) communicate electrical power needed to actuate the valve mechanism via passageway 29. Pneumatic communicating passageways may be substituted as appropriate.

The segments 14, 16 may be joined in a sealing manner as is known to those of skill in the art, including welding or by adhesives. The use of concentric, stepped counterbores on the segments 14, 16 facilitate mechanical alignment of the segments.

Figure 6:
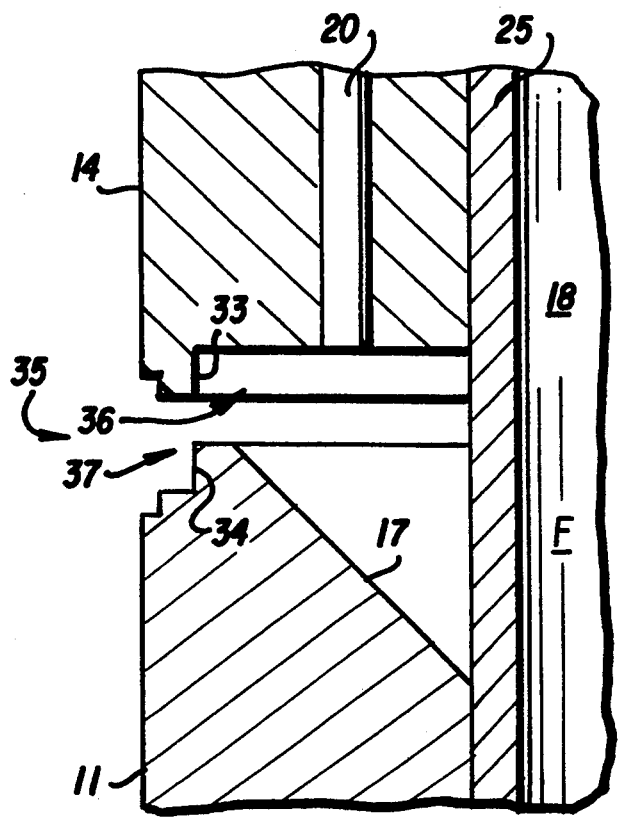
FIG. 6 illustrates a detail of the device of FIG. 5.

Similarly, the segments 11, 14 may be joined by concentric, stepped counterbore features (as are more clearly shown in detail FIG. 6). Attachment of the interior conical reflector segment 11 to the upper main body segment 14 may be effected by a circumferential weld. The sample chamber 18 has a transparent wall 25 disposed between the conical reflector segment 11 and the upper main body segment 14. Prior to joining, the transparent wall 25 (which is a cylindrical section and formed of a strong transparent material such as high strength, high temperature glass), is inserted centrally of these two segments (11, 14) which are then held together with a pressure force suitable for compressing circular or O-ring seals 31, 32 to the desired state of compression for effecting sealing against leakage of the sample fluid. Axial alignment of the reflector segment 11 and the main body segment 14 is accomplished by the mating surfaces 33 and 34 which consist of a stepped counterbore 35 fitted with the main body segment 14 bore 36, the internal diameter of which is no smaller than the external diameter of the step 37 machined into the outside diameter of the reflector segment 11. This mating configuration shown is for illustration only and is not intended to be a limitation of the appended claims, as other equally convenient configurations for aligning and joining the segments known to those of skill in the art may be substituted.

Figure 4:
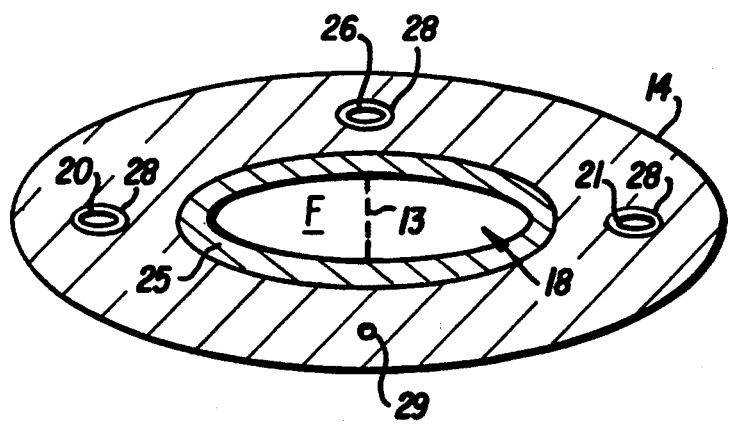
FIG. 4 illustrates a transverse section of the invention, taken immediately below the top seal of the sample chamber, as indicated in FIG. 1.

FIG. 4 reveals the interior section of upper main body segment 14 near the top of sample chamber 18, showing the centerline of segment 14, which is also the axis of revolution 13 of the interior conical reflector segment 11. The first, second, and additional light guides 20, 21, 26 pass through this section. The cylindrical transparent wall 25 forming the sample chamber 18 within the segment 14 includes a plurality of light guide passageways (shown enlarged for emphasis only) 28 surrounding light guides 20, 21, 26 through the segment 14. A further passageway 29 surrounding the electrical/pneumatic communicating passageway to stilling valve actuator segment 12 (not shown in this view) bears the necessary actuation control lines to the stilling valve segment 12.

Figure 5:
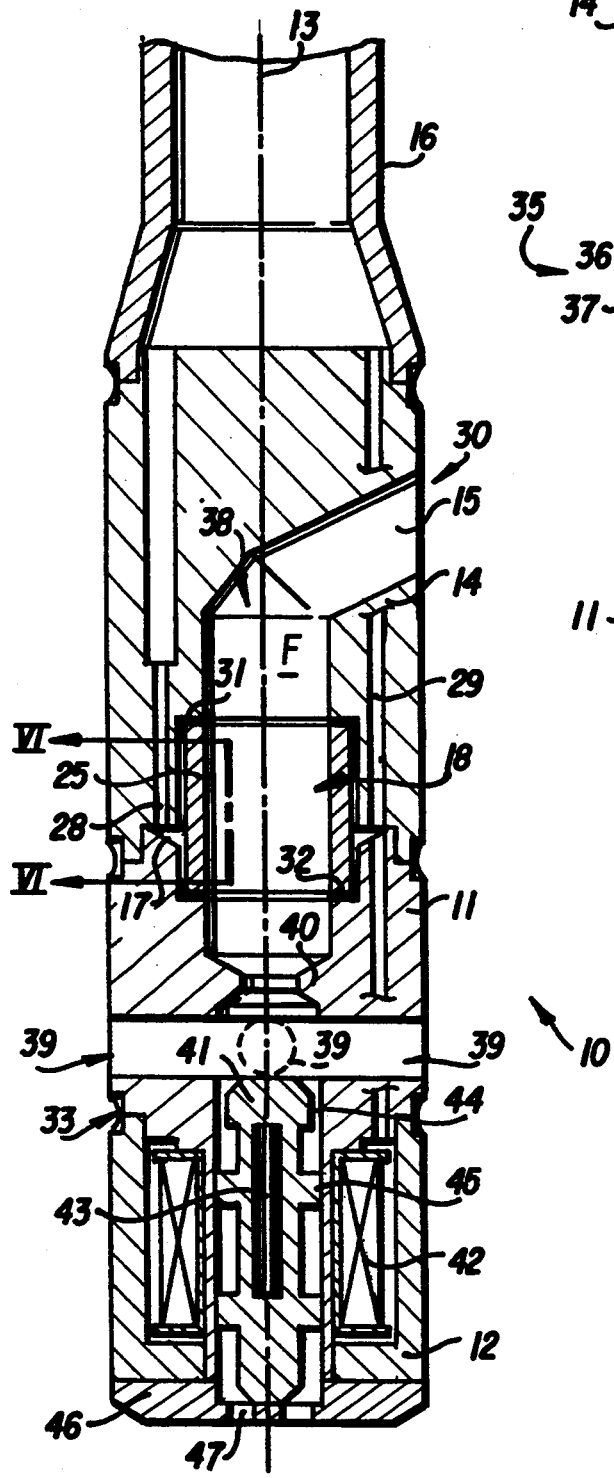
FIG. 5 illustrates a longitudinal section of the invention shown in FIG. 1, further illustrating details of the device.

Turning now to FIG. 5, the reflecting properties and cylindrical symmetry of the conical reflecting surface 17 enable rapid, simple, and comparatively inexpensive manufacture of the novel measurement probe 10 reflector and main body segments 11, 14 incorporating this reflecting surface 17. The segments 11, 12, 14, 16 are disposed along a longitudinal axis which serves as the axis of revolution 13 of the reflector segment 11; an upper vent hole 15 extends upward from the sample chamber 18, defined by a transparent wall section 25, and communicates to the upper port 30, where the sample fluid (F) freely exits from one side of the main body segment 14 above the sample chamber 18. While this embodiment is illustrated by a single such upper port 30, a plurality of such ports may also be employed.

The reflector segment 11 contains one or more process fluid (F) lower ports 39. The lower ports 39 communicate the process fluid (F) directly through the central passageway 38 thence to the upper port 30.

In a preferred embodiment, the reflector segment 11 includes in its lower end certain portions of a valving apparatus which permit the sample chamber 18 to intermittently function as a novel still well as well. More particularly, there is formed in the lower end of the reflector segment 11 a valve seat or stop 40, in the form of a constriction in the cross sectional diameter of the central passageway 38 in the reflector segment 11. The valve stop 40 enables interruption of the free communication of process fluids (F) from the lower port or ports 39 through the sample chamber 18 to the upper port 30 via a vent 15.

A stilling valve actuator segment 12 is responsible for closing the stilling valve formed by the valve seat or stop 40 in the reflector segment 11 and by a plunger 41, which is located in the central passageway of the actuator segment 12. The plunger is sealingly shaped to join with the stop 40 and thus close central passageway 38. Power for actuating the plunger 41 is shown in this example as electro-magnetic via a solenoid coil 42; pneumatic drive means may be substituted such that the plunger 41 closes with the stop 40 by pneumatic pressure. Solenoid coil 42 coacts magnetically with a permanent magnet 43 embedded in the plunger 41, causing the plunger 41 to close the central passageway 38 at the valve stop 40. The plunger 41 preferably includes a plurality of arcuate ridges 44, 45 to ensure proper coaxial alignment of the plunger 41 with respect to valve stop restriction 40. Wires (not shown) communicate the electrical power to actuate the valve mechanism 40, 41 via the coil 42.

The valve actuator segment 12 may be attached to the reflector segment 11 in a manner substantially similar to that in which the reflector segment 11 is joined to the main body segment 14, previously described.

The plunger 41 is retained within the actuator segment 12 by placement of a bottom cover 46 over the lower end of the actuator segment 12; one or more process fluid drain holes 47 may be included in the bottom cover 46 to permit essential drainage and to avoid hydraulic restriction on the free movement of the plunger 41 to close the valve plunger 41 to seat 40.

Figure 2:
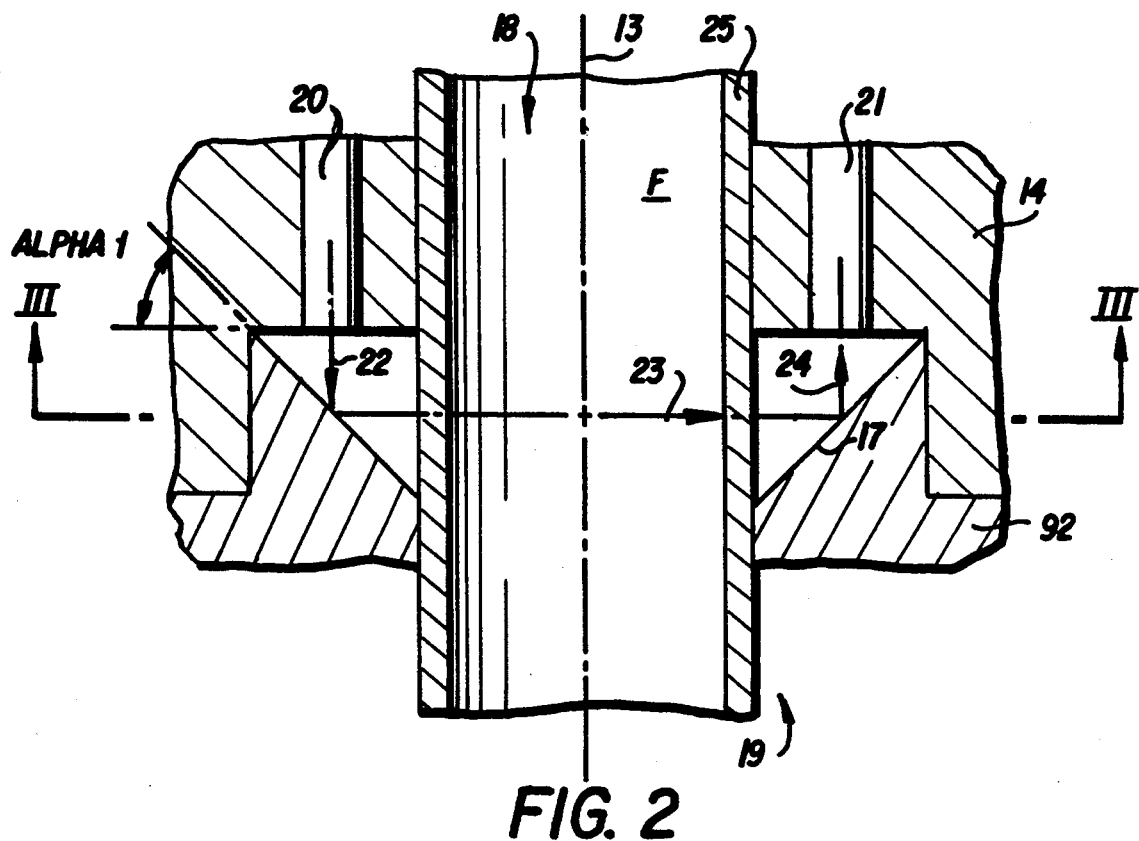
FIG. 2 illustrates in cross-sectional view portions of another optical probe according to a primary aspect of this invention.

A simplified reflector segment is shown in FIGS. 2 and 3. The more basic probe 19 (FIG. 2) having a similar reflector segment 92, the inclination angle alpha 1 of the conical reflecting surface 17 is about 45 degrees in the preferred embodiment. The main body segment 14 houses optical light guides 20, 21, 26. The light guides 20, 21, 26 extend along the length of the main body segment 14, being terminated in close proximity to the reflecting surface 17. Additional light guides 26, 27 may be disposed at various angles relative light guide 20.

A detailed description of the reflector segment 92 relating to light reflecting characteristics of the reflective surface 17 follows, illustrating optical operation of the generic optical probe 19 according to the present invention. Light from a remote source (not shown) is communicated to the probe 19 via a first optical fiber 20. The fiber 20 is positioned in and by the passageway 28 (FIG. 4) in the main body segment 14 and is terminated adjacent the conical reflective surface 17. The conical reflective surface 17 directs this light into and through sample chamber 18, and collects and redirects the light which has been transmitted, partially attenuated, or scattered. Other optical fibers such as the fiber 21 convey the light towards a remotely located radiant energy detector (not shown).

Additional fibers 26, 27 may be positioned off-axis to receive light.

A ray of light traveling along the optical axis of this system, originating in the light guide 20 and transmitted to the light guide 21 is composed of a series of light ray segments 22, 23, 24 for the conical reflector segment 92 having a reflecting surface 17 and an inclination angle of about 45 degrees. The initial light ray portion 22 represents that portion of the light ray leaving light guide 20 and incident on a first surface area of the reflecting surface 17 while the sampling light ray 23 denotes that light ray portion which is reflected through an angle of about 90 degrees and passed through a section of the sample chamber 18 transparent wall 25, where the light sampling ray 23 encounters the test sample fluid (F).

After being passed through the sample fluid (F) and the opposite sample chamber 18 wall 25, the sample ray 23 encounters a second surface portion of reflecting surface 17 and is again deflected through an angle of about 90 degrees to form an exit light ray 24. The light ray segment 24 represents a continuation of the ray 23 from the second portion of reflecting surface 17 to and incident upon light guide 21. FIG. 3 shows the apparatus of FIG. 2 in the plane which contains the light ray segment 23 and which is perpendicular to the axis of revolution 13 of the conical reflector segment 92.

The additional light guides 26, 27 can serve either as collectors of light originating from guide 20 or they can function as light conduits for other external light sources when such are required. When used as light conduits, the additional light guides 26, 27 receive light scattered substantially from the center of sample chamber 18. If the angle alpha 2 is 90 degrees, the configuration is termed nephelometric and the probe may advantageously be used as a nephelometric turbidity probe. The additional light guide 26 collects that light originating from the light guide 20 which light is subsequently scattered by the test fluid (F). The angle Alpha 3 is shown as approximately 55 degrees. In combination, the light guides 20 and 21 permit the measurement of either the forward- scattering component of the turbid media or the attenuation of radiant energy as a function of the number density of dissolved materials in an otherwise homogenous fluid.

Figure 7:
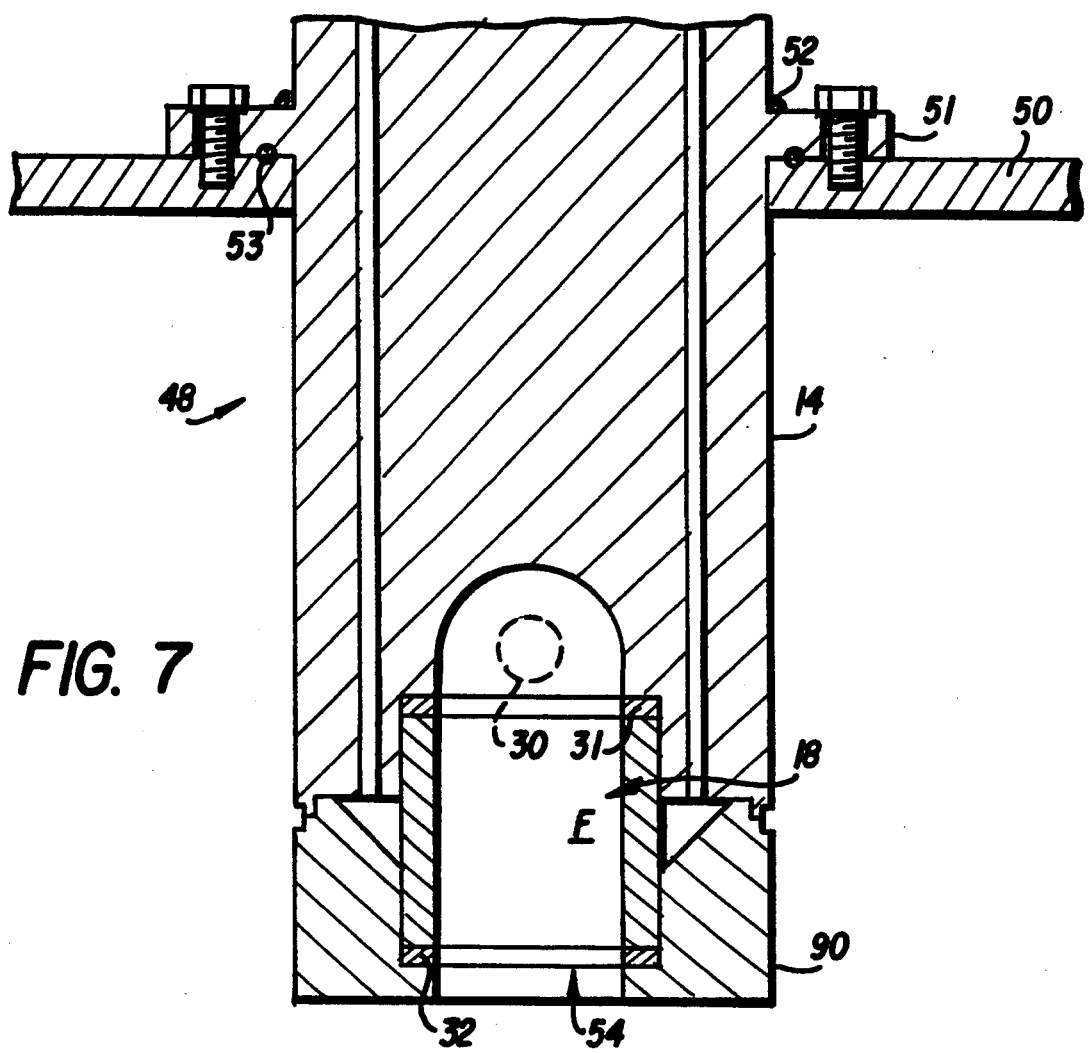
FIG. 7 illustrates a longitudinal section of the invention shown in FIG. 2, wherein the probe is permanently mounted.

Several alternative embodiments of an optical probe using the conical reflective surface are shown in FIGS. 7 through 15. The simplified optical probe 48 of FIG. 7 is adapted for permanent mounting on a vessel, such as a process vessel or storage tank 50, only a portion of which is shown. A peripheral flange 51, attached to the probe 48 (as for example, by a circumferential weld ring 52) illustrates how the probe 48 may be secured to the process vessel 50. A simplified probe similar to the probe 92 shown in FIG. 2 is illustrated. The process vessel 50 may, for example, be a container of fixed size or a pipeline, which can accommodate the length of the probe 48 exposed to the process fluid (F). A sealing means, such as a circular or O-ring seal 53 can be used to prevent the fluid (F) from leaking to the outside environment.

Alternatives for effecting such seals are known to those skilled in the art; the O-ring of this embodiment is not limiting and does not preclude the use of alternative seals. An adequate seal between the sample chamber 18, the reflector segment 90, and the main body 14 may be accomplished with the aid of two O-ring seals 31, 32, glass-to-metal graded seals or the like. These elements may be joined and sealed as previously described. The process fluid (F) is permitted to flow freely through the sample chamber 18 via a lower port 54 and one or more upper ports 30. The measurement process is as previously described; it may be continuous or intermittent with the addition of still well valving apparatus.

Figure 8:
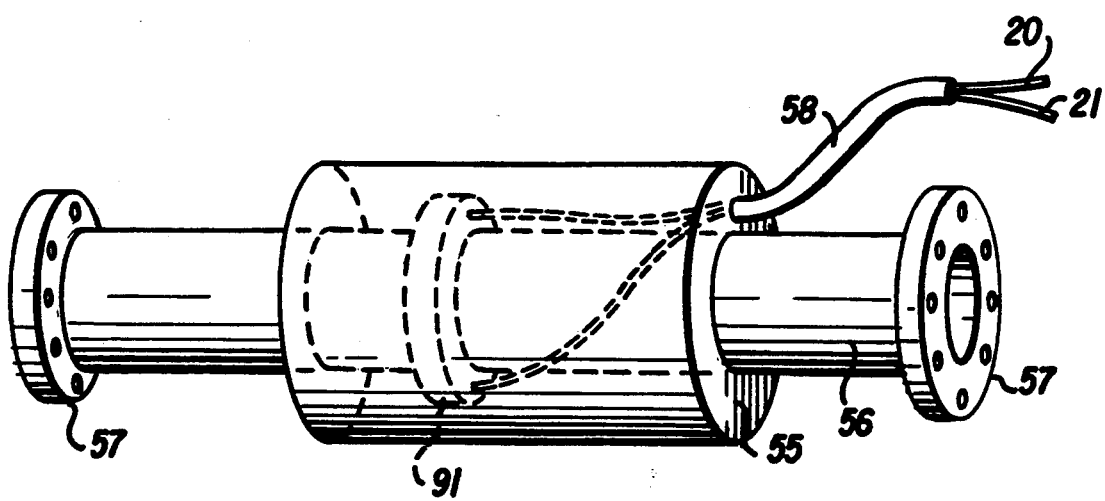
FIG. 8 illustrates the invention shown in FIG. 2, wherein the probe is permanently mounted circumjacent a pipe which may be flanged for insertion in a line.
Figure 9:
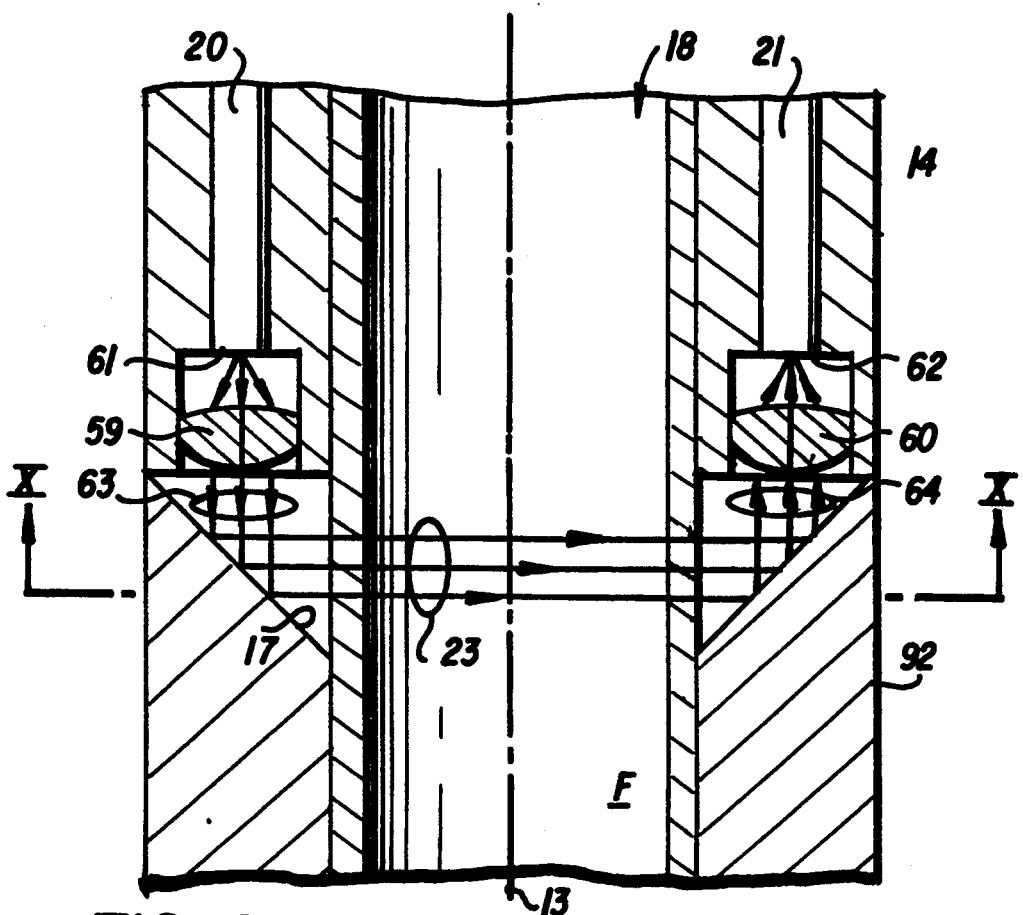
FIG. 9 illustrates an aspect of the invention in which lenses are employed to shape the light beam before and after reflection from the interior conical reflecting surface.
Figure 10:
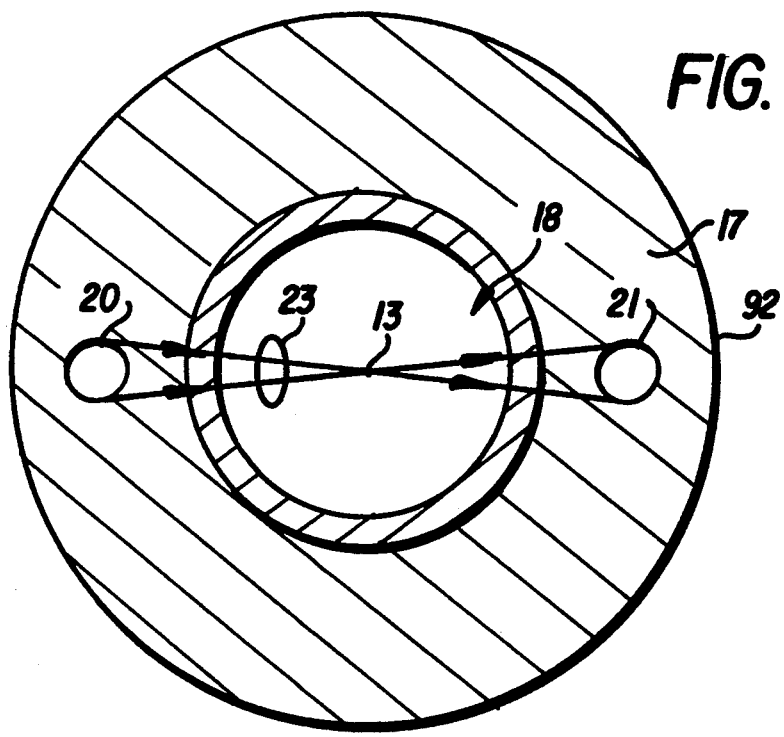
FIG. 10 illustrates another view of the apparatus of FIG. 9.

FIG. 8 depicts another embodiment of the invention. An optical sampling apparatus includes a probe body 55 which contains the conical reflector segment 91 and the light guides 20, 21. It is configured such that the conical reflector segment 91 fits over a pipe section 56 (at least a portion of which is transparent at the sample chamber site) which can in turn be coupled to a sample line (not shown) by one or more end flanges 57. In this embodiment, a single service cable 58 contains all of the optical light guides 20, 21.

Referring briefly again generally to FIGS. 2 and 3, light leaving the light guide 20 includes light rays whose maximum inclination angle with respect to initial light ray portion 22 are determined by the numerical aperture of the light guide 20; all rays having inclination angles less than this maximum inclination angle define an acceptance cone of light which may be transmitted into the light guide 21. Because of this, the plurality of rays striking the reflection surface 17 will result in skew rays through the sample chamber 18, not all of which skew rays will fall within the acceptance cone of the light guide 21 after deflection from the reflecting surface 17 upon exiting the sample chamber 18. This circumstance reduces the maximum radiant energy which traverses the sample chamber. In certain applications, such loss of radiant energy is not serious since one can choose among available light sources, light guides, and radiant energy detectors, the accumulated sensitivities and losses of which, when combined, yield a favorable measurement sensitivity.

A further improvement of the embodiment of the invention depicted in FIGS. 2 and 3 addresses the decreased measurement sensitivity situation described above; the optical scheme of FIG. 9 promotes more efficient transfer of light through the sample chamber 18. Additionally, this embodiment results in optical rays the passage of which through a test fluid (F) is affected less by changes in the refractive index of the fluid, such as might result from changes in temperature for example.

Specifically, the individual lenses 59, 60 are interposed between the ends 61, 62 of the light guides 20, 21, respectively. The lens 59 serves to substantially collimate the light leaving the light guide 20 and the collimated beam is in turn imaged (by the reflecting surface 17) at the center of the sample chamber 18, substantially independent of the index of refraction of the test fluid (F); this is shown even more clearly in FIG. 10, where the sampling light ray 23 is perpendicular to the axis of revolution 13 of the reflector segment 92. The incoming light rays and outgoing return light rays are represented collectively as light beam diameters 63, 64, respectively. The return light beam 64, incident on the lens 60 is re-imaged onto the end (i.e., input face) 62 of the light guide 21. The longitudinal line image, formed at the center line (or axis of revolution 13 of the reflector segment 92) of the sample chamber 18 has a length substantially equal to the diameter 63 (and also the diameter 64).

Figure 11:
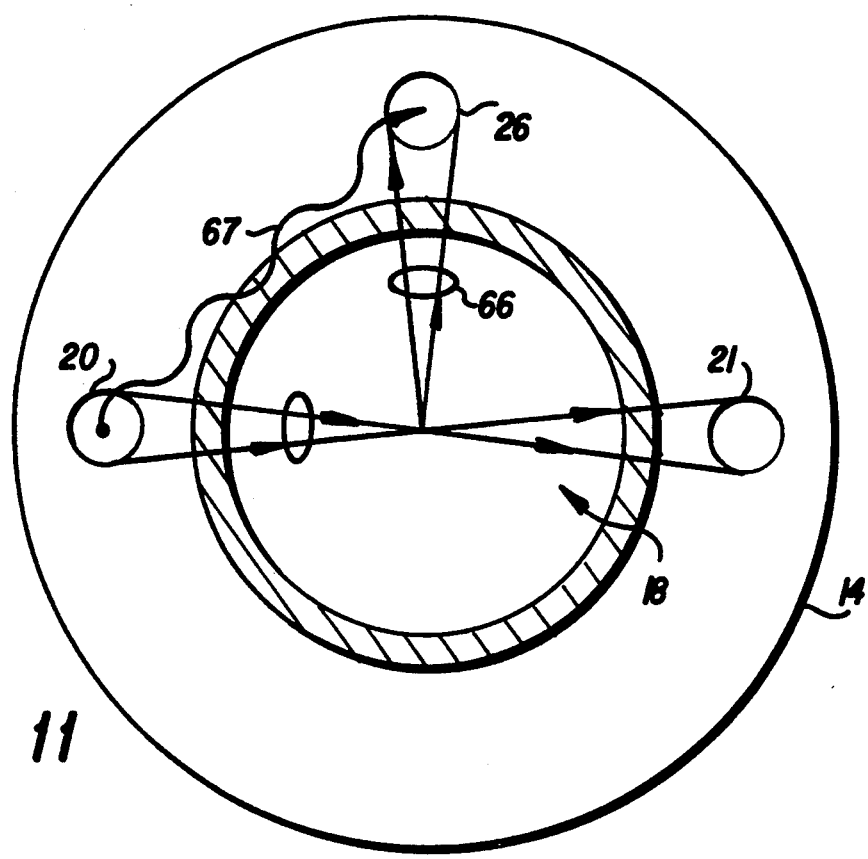
FIG. 11 illustrates in plan view another aspect of the invention which solves the potential problem of stray light.
Figure 13:
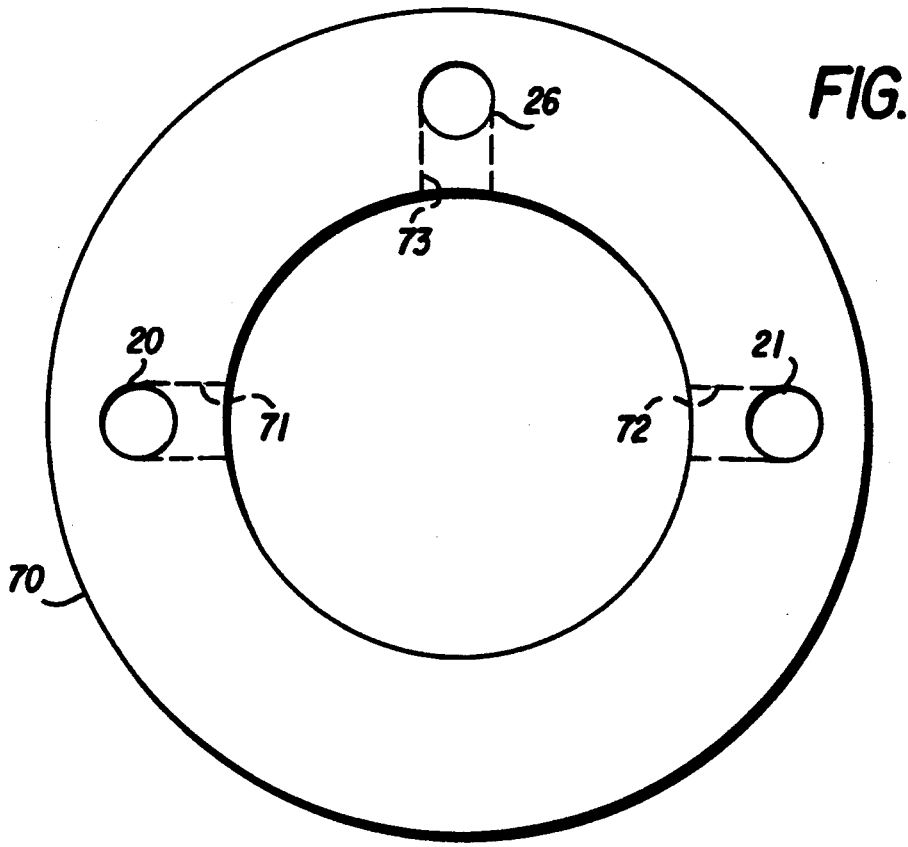
FIG. 13 illustrates another view of the baffle according to FIG. 11.
Figure 12:
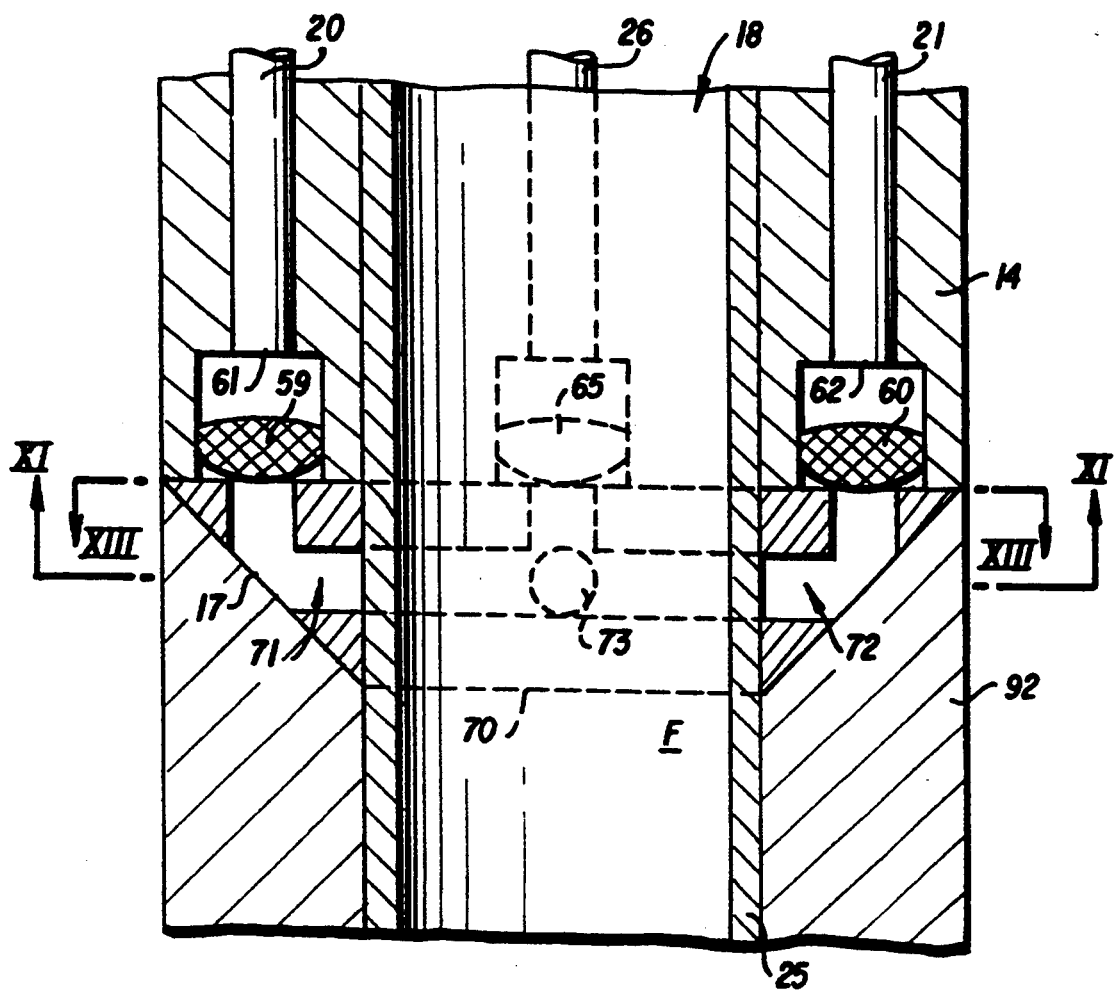
FIG. 12 illustrates in longitudinal section view the baffle of FIG. 11, incorporating apparatus similar to that of FIG. 2.

In certain uses it will be desirable to eliminate or reduce stray light. Those of skill in the art will appreciate that a limitation to many optical-based measurement systems is the presence of stray light, which by definition, is that light which reaches the detector by paths other than that intended. As an example, in turbidity measurements, excessive stray light may limit sensitivity when analyzing for low levels of suspended matter. One way to minimize sources of stray light in an optical probe is shown in FIGS. 11, 12, and 13. A stray light baffle 70 may be used to eliminate or reduce stray light. Such a baffle 70 limits the angle of passage of light through the test chamber 18 wall 25.

An additional light path via the lens 65 is positioned approximately normal to the optical axis (defined by the light ray 23 in FIGS. 2 and 9) and passing through the center of the sample chamber 18. This configuration may be employed for measuring very low turbidity levels, but may also be appropriate for Raman spectroscopy. A portion of the light scattered by matter in the sample fluid (F) volume near a point, for example the centerline and axis of revolution 13, is directed towards the collection lens 65. The light rays 66 comprise this light. Stray radiation such as that indicated by a wavy line light ray 67 may also reach the lens 65 if the conical reflecting surface 17 is not perfectly smooth, so that light incident upon it from the lens 59 may be scattered by surface defects into many directions, only one example of which is illustrated by the wavy line light ray 67. One of ordinary skill will appreciate that the light ray 67 does not actually travel in the curvilinear fashion indicated but rather is illustrative in nature. The presence of such rays reaching the collection lens 65 and from there via the light guide 26 to the appropriate detection means (not shown) implies that in the absence of any scattering material in the test chamber 18, a finite signal is produced. This signal, if large enough, can adversely limit the sensitivity of the device and make a precise measurement of low concentrations quite difficult.

To eliminate this difficulty, a circular light restricting baffle 70 including a plurality of radially extending passageways 71, 72, 73 is interposed between the reflective surface 17 of the reflector segment 92 and the main body segment 14, which latter segment contains the lenses 59, 60, 65 and the respective light guides. Baffle 70 includes a passageway 71, which permits light from light guide 20 to pass unobstructed into sample chamber 18 after collimation by lens 59. Another radial passageway 72 permits the directly transmitted beam to pass through unobstructed to the lens 60, and a third radial passageway 73 of the baffle 70 permits light scattered by the sample to pass on further to the lens 65. However, baffle 70 prevents stray light rays such as the stray ray 67 from reaching the lens 65 except via the baffle 70 passageways 71, 72, 73 and the sample chamber 18. A plan view of the baffle 70 is shown in FIG. 13. By varying the size and shape of the passageways created in the baffle 70, it is further possible to control such factors as how much light is collected by the lens 65 for purposes of controlling the collection angle of light.

Figure 14:
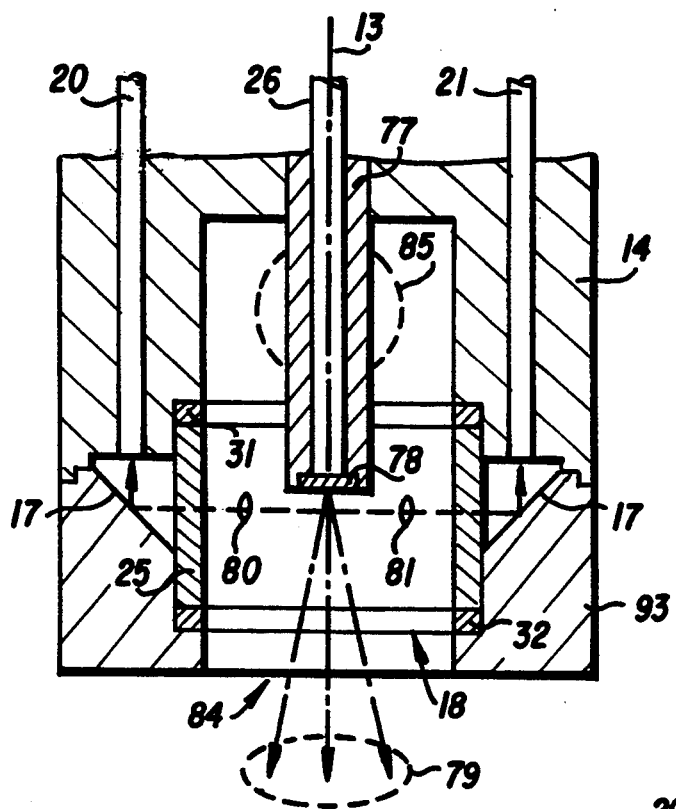
FIG. 14 illustrates an aspect of the invention in which radiant energy is introduced directly into a sample test chamber and scattered radiation is collected by the interior conical reflector element.

FIG. 14 illustrates yet another embodiment of the invention whereby light is introduced along the longitudinal central axis 13 of the cylindrical sample chamber 18; that light which is scattered at 90 degrees is collected by the reflecting surface 17 and directed towards one or more receiving light guides, illustrated by the light guides 20, 21. Here, the light guide 26, contained within a protective sheath 77 carries light to the sample chamber 18 where it passes through a protective, transparent window 78. The light beam 79 emerging from the window 78 is scattered at various angles. The assembly and construction of the configuration illustrated in FIG. 14 is substantially the same as that previously described except that the incoming light is introduced along the longitudinal axis and collected normal thereto. In particular, the light rays 80 and 81 illustrate light rays which have been scattered at about 90 degrees with respect to the incident light beam 79 by the test fluid (F). The approximately 90-degree scattered radiation is directed towards a plurality of collecting optical fibers 20, 21 by conical reflector segment 93 reflecting surface 17. Here, segment 93 is open-ended and truncated to permit free flow of the sample into the sample chamber. Again, the sample chamber 18 is disposed between the O-ring seals 31, 32 while a lower port 84 and an upper port 85 permit free exchange of test fluid (F) within the sample chamber 18. A lens could be interposed between the light guide 26 and the window 78 (or substituted for window 78) whereby the shape of the outgoing beam 79 could be adapted to a wide variety of measuring requirements; thus the point of maximum energy concentration within light beam 79 could be extended further beyond window 78 by suitable choice of lens power.

Figure 15:
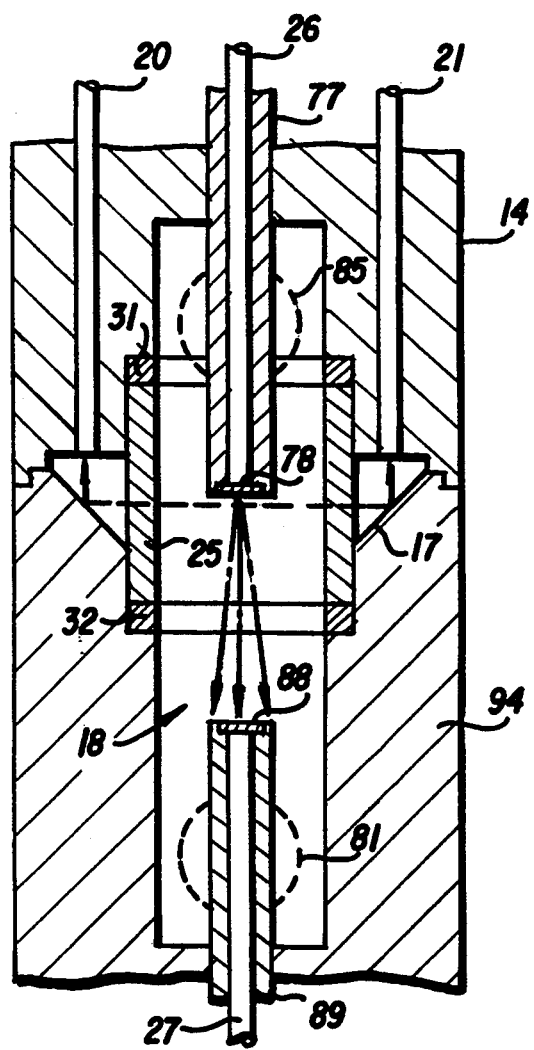
FIG. 15 illustrates alternative apparatus in which radiant energy is introduced directly into a sample test chamber and scattered radiation is collected by the interior conical reflector element.

A still further embodiment of this present invention is disclosed in FIG. 15, where light is introduced along the longitudinal axis and in which transmitted radiant energy may be collected by at least one additional light guide 27, as well as scattered light being collected by light guides 20, 21. In this case, the sample chamber 18 is self-contained and an additional port 87 is added to permit the test fluid (F) to flow through the sample chamber 18. The assembly and construction of the configuration illustrated in FIG. 15 is substantially the same as that previously described. Reflective segment 94, however, is closed below port 87.

Thus, as described above, this invention provides a method and apparatus for simplifying the introduction of light into and from a sample chamber for the purposes of monitoring changes in the transmitted, attenuated, or scattered radiant energy passed through the sample chamber.

Another embodiment of the probe is illustrated in FIGS. 16–20. Externally, the optical probe 100 is similar to probe 10 of FIGS. 1 and 5 with improvements to segment 102 and a cover 104 therefor, and improvements to the main body 106, incorporating therein the function of both segments 14 and 16 of FIGS. 1 and 5 in a single integral unit. An additional improvement in manufacturability results from sealing the segments with O-ring seals and joining the segments relatively permanently, but separately, with strong adhesives. The cross sectional profile of probe 100 varies from that of probe 10 in FIGS. 1 and 5, becoming progressively smaller, rather than larger, towards distal end at segment 102. The probe internals are shown in greater detail in FIG. 17, wherein main body 106 houses a pair of wires 108 joined to electrical-to-optical transition stage 110 or alternatively an optical pathway 112 is connected to optical-to-optical transition stage 114. Optical pathways contained within protective tubes 116 and 118 respectively, efficiently carry the optical signal to and/or from the test chamber, as described hereinafter. Main body 106 is preferably cylindrically shaped about a longitudinal axis (axis 120 of FIG. 20) for easy entry into an aperture in the line or vessel wherein the sample fluid is measured. An O-ring seal 122 is provided in peripheral groove 124 for sealing the instrument in the aperture. Other sealing structures may be substituted, as known to those of ordinary skill in the art.

The segments 106, 102, and cover 104 are preferably made of stainless steel or an equivalent strong, durable, and corrosion-resistant material; they are elongated, and cylindrical in shape, and preferably incorporate matching concentric, stepped counterbores 126, 128, and 130, 132 as indicated at 134, 136, and 138. Axially spaced along these counterbore junctions are suitable grooves for holding a series of O-ring seals 140, 142, and 143, or such equivalent seals as are known in the art. Cover 104 may be assembled over segment 102 before or after joining segment 102 to main body segment 106.

The segments 106, 102, and cover 104 may be joined together at sites 134, 136, 138 in a sealing manner as is known in the art; adhesives are preferred, although threaded components or welding may also be used. Sealants and threaded members more readily enable removal for maintenance operations. However, sealants must be carefully selected, giving due consideration to the materials selected for the segments 106, 102, and cover 104, to the temperatures which the probe is to be subjected in use, and to the fluids in which the probe will be immersed. Specifically, one part, oven-cured, expoxy bonding adhesives such as Uniset ® 1962-31 sealant, from Emerson Cuming, are suitable. This adhesive bonds stainless steel, and is believed acceptable for long-term contact with food and drugs.

The segments may be separated after sealing by subjecting the sealant to its release agent or by heating the joint above the temperature at which the sealant breaks down. The release agent for Uniset ® 1962-31 sealant is ECCOSTRIP ® 93 from the same manufacturer. The breakdown temperature of Uniset ® 1962-31 sealant is above 800° F. It is an important advantage of the present embodiment that, by increasing the optical efficiency of the probe, the need for electronics amplification and signal processing stages located within the probe has been substantially eliminated, permitting the heating of the sealant adhesive to these high temperatures. That is, absent the present optical improvements, electronics circuitry which would otherwise likely be necessary is avoided, making it possible that the probe joints can be heated above those temperatures at which electronics packages normally fail.

Joining by use of threaded segments requires careful alignment such that longitudinal passageways are properly aligned. Welding maximizes difficulty in maintenance and repair as it becomes difficult to enter the probe cavity.

Main body segment 106 includes a generally longitudinal main passageway forming an interior cavity 146 which is terminated in an end wall forming cavity bottom 148 and smaller longitudinal passageways 150 and 152 to guide the respective optical pathways to the sample chamber area, as will be described subsequently. The main body 106 also includes a fluid passageway terminating in at least one exterior upper vent hole 154 similar to upper vent hole 15 in FIGS. 1 and 5. One or more additional longitudinal passageways for additional optical pathways (shown in FIG. 20) may also be included. One or more longitudinal electrical wire or pneumatic passageways are required when a stilling valve is included, as in segment 102 of the present embodiment illustrated in FIGS. 16–20. Another segment, not shown, may be joined to main body 106 with the internal threads 156 at the extreme proximal end. A seal 158, such as an O-ring seal, may be used to seal this segment to main body 106. While it is noted that the main body cavity may be large enough to hold electronics circuitry or the like, the present design specifically succeeds in increased sensitivity in order to eliminate the use of such temperature sensitive additions to the probe.

Segment 102, attached at the distal end of probe 100 and facing the main body segment 106 includes, according to the embodiment of FIGS. 16–20, an integral interior conical reflecting surface 160 formed in the proximal end of segment 102. This surface 160 is of a shape which is substantially similar and functionally equivalent to the formation of the interior conical reflecting surface 17 of the first embodiment, as seen for example in FIG. 6. However, the manufacturability of the interior conical reflecting surface 17 and the precise alignment thereof during assembly has been significantly enhanced in the embodiment of FIGS. 16–20 by forming the interior conical reflecting surface 160 as an integral element of segment 102. Surface 160 is formed in the proximal end of segment 102. Spaced from the surface 160 towards the distal end of segment 102 is a peripheral groove 162 about the longitudinal axis of the segment. This groove carries the solenoid coil 164 winding when an electrical solenoid stilling valve is used, as described in greater detail hereinafter. An axial bore 166 extends the full length of segment 102, and communicates with the distal end of the sample chamber and with upper vent hole 154 in main body 106 at its proximal end. Axially spaced along this bore and longitudinally spaced a short distance from the sample chamber is a necked-down area which provides a valve seat 168 for the stilling valve included in this illustrative example, and which is substantially similar to valve seat 40 of the first embodiment.

Main body segment 106 includes a central recessed bore in the distal end thereof adjacent segment 102 for enclosing the transparent chamber wall cylinder 170, which may be of glass or such other material as described earlier in connection with FIGS. 1–15. The cylinder 170 is positioned radially by the aforementioned bore and by respective proximal and distal O-ring seals 172 and 174, which tightly seal the chamber and position cylinder 170 therebetween. Details of this configuration are described above in association with the embodiments described in FIGS. 1–15. Other seals may be substituted as known to those skilled in the art.

The stilling valve actuator is responsible for closing the stilling valve formed by the valve seat 168 or stop and by a plunger 176, which is located in axial bore 166, the central passageway through segment 102. The plunger 176 is sealingly shaped to join with the seat 168 and to thus close axial bore 166. Motive power for actuating the plunger is shown, in this example, as being provided electromagnetically via a solenoid coil 164; as with the embodiments illustrated in FIGS. 1–15, pneumatic drive means (not shown) may be substituted such that the plunger 176 closes with seat 168 by pneumatic pressure. Solenoid coil 164 coacts magnetically with a permanent magnet end 178 of the plunger 176, causing the plunger to close the axial bore 166 central passageway at the valve seat 168.

The source of the magnetic force may be contained within plunger 176 as shown in the first embodiment (FIG. 5) or may be or include a magnetized region, such as plunger ridge 178. The plunger 176 preferably includes one or more radial ridges 178, 180, 182 to ensure proper coaxial alignment of the plunger with respect to the valve seat restriction. Wires (not shown) communicate between coil 164 and a power source external to the probe to actuate the valve mechanism via the coil 164; the wires pass through the probe as shown in FIGS. 1–15.

An ordinary coil spool cannot be used to retain and protect the winding in the configuration shown in FIGS. 16–17; since thinly insulated wires are required, one or more lengths of protective insulation padding, such as insulated tubing, may be used to protect the winding entry and exit turns from shorting to the body of segment 102.

The plunger 176 is retained within the distal end of segment 102 by a threaded adjuster 184. Adjuster 184 includes a plurality of external threads which mate with threads 186 inside the distal end of segment 102; one or more longitudinal fluid passageways can be provided through adjuster 184 to permit relatively free fluid entry into the sample chamber stilling well. Deep longitudinal grooves can also be used for this purpose. While such passageways are preferred in this example, the present invention is not to be limited thereto. Such free fluid flow permits essential drainage and avoids hydraulic restriction on the free movement of the plunger to close the valve plunger to its seat. A plurality of communicating fluid passageways 188 are used, as seen in FIGS. 16 and 17, to permit free fluid entry and exit into the plunger chamber and into the sample chamber.

The respective top and bottom drain ports 154 and 188 function as described to promote free exchange of the test chamber fluid contents with the bulk sample. This arrangement leads to several sampling advantages. As with the embodiments of the invention illustrated in FIGS. 1–15, the enclosed chamber prevents large disruptions of the optical beam either by entrained air or by fluid level fluctuations such as may occur due to rapid stirring of the sample. Second, bubbles which do pass through the enclosed chamber shutter the optical beam for only a brief period; use of the stilling scheme is effective in minimizing these disturbances. In some mounting configurations, the main chamber wall can be disposed parallel with the fluid flow; there is thus little tendency for bubbles to accumulate on these surfaces, which would otherwise lead to erratic reductions in the dynamic range of the measurement. The stilling valve is otherwise effective in minimizing these bubbles. Accumulated solid matter may be removed by cleaning when needed.

Fluid flow for operation of the probe is substantially as described previously in connection with FIGS. 5, 7, and 10. The probe 100 can often be disposed such that the optical path through the fluid lies in a plane perpendicular to the flow of fluid within the sample chamber, i.e., the longitudinal axis of the probe. The subject fluid is passed then through the probe 100. Shortly before a sample is to be taken and measured, the stilling valve solenoid is actuated by passing an electrical current through the solenoid coil 164 such that the magnetic field of the plunger magnetic end 178 and the electromagnetic field of the coil interact to force the plunger 176 against its seat 168 to close the stilling valve and seal off the sample chamber. Alternatively, a pneumatic pressure force variation can be used to close plunger 176 against its seat 168. In either case, entrained bubbles are then free to float out of upper vent hole 154 without additions thereto and solids are permitted to settle out of the optical path in the test chamber.

The embodiment of the invention shown in FIGS. 16–20 includes improvements in the operation of the stilling valve mechanism; the structure of the first embodiment was found to be especially sensitive to set up and adjust for proper closure of the valve, both initially and especially following maintenance operations such as cleaning. This adjustment difficulty was found to be at least partly related to variations in the strength of the magnet 43 shown in FIG. 5. The interaction of the electromagnetic field produced by the coil 42 and the permanent magnet 43 field achieved less reliable valve closing forces than desired in some cases when adjustment was improper. In the present embodiment this variation in valve closing force is accommodated by making the rest position of the plunger (and thus the axial distance of travel thereof to seat 168) variable.

Correction of this difficulty contributed to greater manufacturability of the probe 100. This seat position adjustment is accomplished simply by inserting a small flat blade such as a screwdriver tip into slot 190 in the distal end of threaded adjuster element 184 and turning the adjuster in axial bore 192 within the threaded interior portion of bore 192 to position plunger 176 as desired relative the coil 164. This adjustment enables the assembler to easily and rapidly select a desired plunger rest position within a range of acceptable plunger positions which provides reliable operation.

Figure 18:
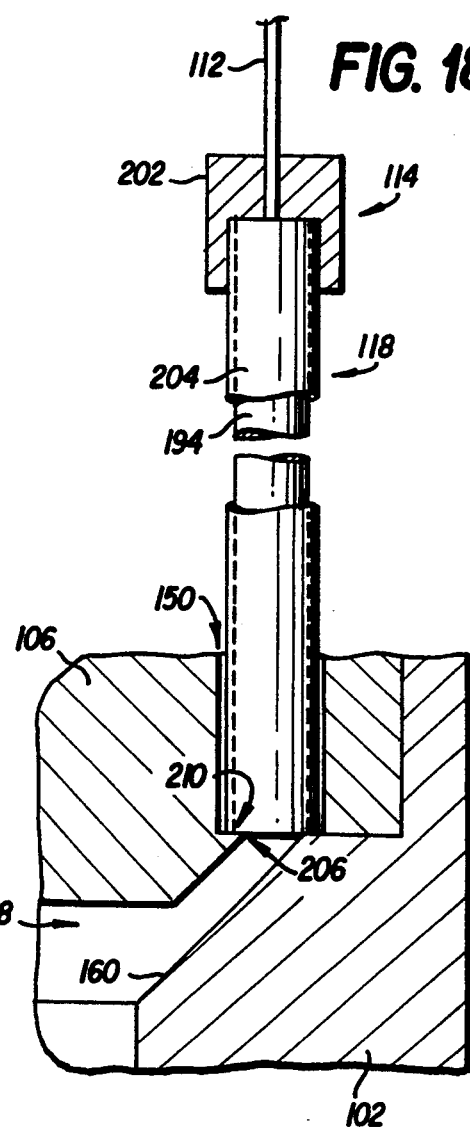
FIG. 18 illustrates electro-optical sensing and detection and positioning of the optical rod relative the reflective surface according to a variation of the probe of FIG. 16.
Figure 19:
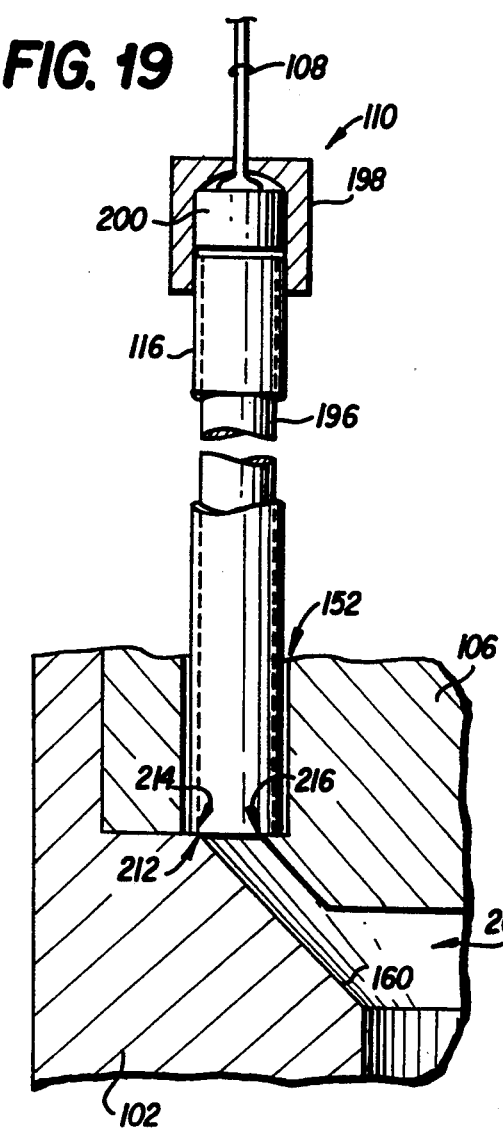
FIG. 19 illustrates entirely optical sensing and detection and positioning of the optical rod relative the reflective surface according to another variation of the probe of FIG. 16.

In the embodiments of FIGS. 1–15 previously described, optical fibers carry the optical signal to and from the internal conical reflecting surface through the main body. Considerable difficulty arises in precisely aligning the tiny optical fiber relative the internal conical reflecting surface. The optical fibers must be quite precisely positioned both axially and radially within the probe, and securely held in place against movement. In the present invention, both of these difficulties are corrected by substituting a large diameter, rod-shaped optical light pipe of considerable greater diameter, and which also has more efficient optical energy transfer characteristics. Thus there is shown in FIGS. 18 and 19 two illustrative variations of the present invention in which either combined electro-optic or solely optical sensing and/or detection may be used. The improvements of the present invention considerably increase the facility with which the light pathways and the internal conical reflecting surface may be precisely aligned and maintained in such alignment.

For convenience, applicants prefer the electro-optical sensing/detection scheme used in FIG. 19, rather than the solely optical system of FIG. 18. The two variations may be combined, with one serving as a sensor and the other as a detector, as may be desired in some circumstances. FIGS. 18 and 19 also illustrate alternate variations in positioning the end of the optical rods 194, 196 with respect to the reflective surface 160.

FIGS. 17 and 19 illustrate the preferred variation of the invention in which wires 108 carry the optical sense signal to the probe 100 or alternatively convey the detected signal from the probe. An electrical-to-optical transition stage 110 contained within the probe 100 main body 106 interior cavity 146 includes a cup-shaped cap 198 housing a transducer 200 which is either an electrical light source or an opto-electric device for converting optical energy into electrical energy, as described hereinafter. Also inserted into the cap 198, and preferably communicating with the transducer for maximum energy conversion efficiency, is the proximal end of an elongated optically transmissive rod 196, such as a glass rod. These rods are sized between 0.001 and 0.100 inches and preferably about 0.062 inches, as opposed to the approximately 400 micrometer fiber optic diameters disclosed in FIGS. 1–15. Suitable other materials may be substituted, as known to those of ordinary skill in the art. The rod 196 is carried by a protective and shielding tubular guide 116, which may also extend at least partly into the cap 198 if desired. The distal end of the rod is positioned adjacent the internal conical reflecting surface 160 as described hereinafter. Tube 116 carries rod 196 through the elongated passageways 152, etc., previously described to a point adjacent the internal conical reflecting surface 160, which as previously described is formed in the proximal end of segment 102.

In the FIG. 19 variation of the present embodiment, electrical wires 108 communicate the sensing signal to the probe 100. The same configuration may be used to detect the sensed signal and convey it externally by wires; the difference between the sense and detector configurations being that in the sense configuration, an electro-optical transducer, or light source is required, while in the electrical detector configuration, a light-to-electrical current transducer is required. In practice, a light-emitting diode (LED) can be used as the light source; an infrared or laser LED may be preferred in some measurement schemes. Alternatively, photodiodes can be used. The wavelength of the light source can be selected for a desired wavelength for such measurements as are determined to be wavelength-sensitive. Examples of detector transducers include photocells, phototransistors, and their equivalents.

In operation according to the FIG. 19 configuration, a transducer 200 converts light energy to electrical energy or electrical energy to light energy when used in the detector or sense configuration, respectively, and an electrical signal is communicated between a remote site and the transducer 200 via wires 108.

The variation shown in FIG. 18 is an all-optical version generally similar to that of the FIGS. 1–15 embodiment with significant improvements to the mechanical alignment and optical path efficiency characteristics. Here, a given optical path between the reflecting surface 160 and the optical fiber 112 may serve as either an sense or detect path, as depends on the hardware connected to the remote end of the optical fiber 112. Thus FIG. 18 serves in describing both functional uses: sense and detect, the difference being the source and direction of the light. As a sense optical pathway, optical fiber 112 carries the optical sense energy to a cup-shaped cap 202. A simple optical-to-optical transition stage 114 is contained within the probe 100 main body 106 interior cavity 146. Transition stage 114 includes a cap 202 which houses, and preferably contacts the optical fiber end for maximum transfer efficiency, and the proximal end of an elongated optically transmissive rod 194, such as a glass rod similar to rod 196 previously described. Again, suitable other materials may be substituted, as known to those of ordinary skill in the art. The rod 194 is carried by a protective and shielding tubular guide 204, which may also extend at least partly into the cap 202 if desired. The distal end of the rod is positioned adjacent the internal conical reflecting surface 160 as described hereinafter. Tube 204 carries rod 194 through the elongated passageways 150, etc., previously described to a point adjacent the internal conical reflecting surface 160, which as previously described is formed in the proximal end of segment 102.

FIGS. 18 and 19 also illustrate alternate variations in positioning the end of the optical rod 194, 196 with respect to the reflective surface 160.

At the distal end of segment 106 in FIG. 18, rod 194 is stopped from extending past peripheral abutment 206, which extends radially outward to precisely position the tip of rod 194. A cavity 208 is formed by the depression formed by internal conical reflecting surface 160, machined or otherwise formed in the proximal end of segment 102; it is closed by the distal end of segment 106. By forming the distal end of segment 106 in a convex shape, the volume of this cavity 208 may be reduced; by extending the edge radially over the edge of the passageway 150, the rod 194 is precisely positioned when inserted fully into passageway 150. The convex extension thus serves a two-fold purpose: reducing the cavity volume and precisely positioning the rod 194.

A very small amount of sealant/adhesive may be applied at the conjunction of rod 194 and tube 204 at sealant location 210 in contact with abutment 206 to restrain movement of the rod 194 and/or tube 204 to one place. The cooperation of elements 204, 194, 210, 202, and 206 greatly improves the ease of assembly and the long-term reliability of the relative position of the optical rod 194 and internal conical reflecting surface 160, and thus the functioning of the entire probe.

In FIG. 19, a radially inward extending surface joining the proximal termination of segment 102 forms a rod stop 212 preventing further extension of the optically transmissive rod 196 towards reflecting surface 160. More particularly, the terminal end 214 of rod 196, i.e., the rod tip, is prevented from further movement towards reflecting surface 160 by rod stop 212. An additional rod stop surface 216 may be used if desired, or omitted. Rod stop 216 is substantially similar to rod stop 206 of FIG. 18, described hereinbefore. Note that the radial lip formed at 216 may be partially removed at the site of rod 196 light path communication with the internal conical reflecting surface 160, in order permit the light beam to freely pass between the rod 196 and surface 160.

Shield 116 guides and protects rod 196 between the cap 198 and the reflecting surface 160 and through passageway 152. Rod stop 212 precisely positions and limits movement of the rod with respect to the reflecting surface 160; the additional rod stop 216 may alternatively be positioned at the distal end of segment 106 for this purpose.

Cavity 208, formed by the depression formed by internal conical reflecting surface 160, is closed by the generally convex distal end of segment 106. The cavity volume is thus minimized.

Significant light path improvements within the chamber have been rendered possible by the foregoing structural improvement illustrated in FIGS. 15–19. The improved light path, and the more precise positioning of the light path carriers—rods 194, 196—greatly increases efficiency.

Linearity and sensitivity of reflectance measurements are also improved with changes in the port angles relative one another. The addition of an optical immersion fluid to the cavity has been found to significantly increase optical transmission and thus sensitivity within the cavity 208.

Figure 20:
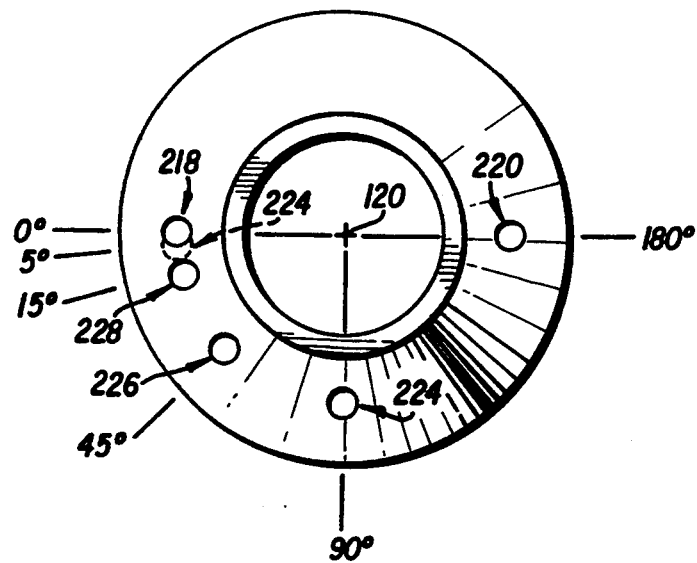
FIG. 20 is an illustrative cross section of the probe showing the relative positioning of the sense and plural detection pathway positions, and location of the stilling valve power communication passageway.

In the embodiment of FIG. 4, the sense (input) light port 20 and detect (output) light port 21 to and from the chamber 18 are displaced oppositely at a 180-degree angle, and the reflectance detection light port 26 for detecting light reflected within the chamber 18 is normally displaced at a 90-degree angle between light port 20 and light port 21. As shown in FIG. 3, an angle (Alpha 3) is disclosed for this purpose which is less than 90 degrees, but greater than about 50 degrees. FIG. 20 is a composite view showing for comparison the main relative port positions for the FIG. 4 embodiment and also those for the present improvement.

In the presently disclosed embodiment of FIGS. 16–19, as illustrated in FIG. 20, the sense port is located at 0 degrees, position 218 and the detect port is located at 180 degrees, position 220, generally corresponding to the position of light guides 20 and 21 of FIGS. 3 and 4. The reflection port of FIGS. 3 and 4 is shown at 222. The reflection port of the present disclosed embodiment is displaced within a range of from about 5 degrees at position 224 to less-than about 45 degrees (relative the sense light, 218) at position 226, preferably within a range of about 5 to about 30 degrees. The angle is more particularly preferred at between about 5 degrees (position 224) and about 20 degrees, or within a narrower range centered around about 15 degrees (position 228). In FIG. 20, the minimum angle for locating a reflectance port at 224 is given at 5 degrees; the actual size of the light rod is increased for emphasis, thus locations 218 and 224 are shown as overlapped when in actuality they would lie adjacent, but separated from one another.

The invention is not to be limited by the illustrative, preferred embodiments disclosed herein. Numerous modifications and variations will be apparent to those skilled in the art. Other equivalent light communications pathways may be employed; equivalent materials may be substituted; and equivalents of the particular methods of forming parts disclosed may be employed without departing from the spirit and scope of the present invention as claimed in the appended claims.

What is claimed is:

1. A probe for optically-based sampling comprising:
   a) an elongated main body having a recessed distal end;
   b) an elongated extension body adapted for attachment to said main body, having an interior conical reflecting surface facing said main body;
   c) a sample chamber disposed between said extension body and said main body in said main body recess, said sample chamber further including an optical entry and an optical exit, and a fluid entry, wherein the sample chamber is adapted to contain a fluid;
   d) means for directing radiant energy from an external source to a first node located within said main body;
   e) means for communicating radiant energy from said first node to a first portion of said interior conical reflecting surface, comprising a first conducting rod;
   f) means for communicating radiant energy from said first portion of said interior conical reflecting surface to a detector; and
   g) means for admitting successive samples of such fluid into said sample chamber wherein said means for admitting comprises an extension body central chamber which includes a necked-down portion of reduced cross section, and said means for admitting comprises means for closing said chamber at said necked-down portion.

2. The probe of claim 1, wherein said extension body includes a recessed bore positioned between a first end thereof which joins said main body and said interior conical reflecting surface which is formed in said extension body.

3. The probe of claim 1, wherein said first node comprises transducer means for converting electrical energy in a first medium to optical energy in a second medium.

4. The probe of claim 1, wherein said first light conducting rod is a discrete rod enclosed within a first rod casing.

5. The probe of claim 4, further including a second node location within said main body interposed between a second portion of said interior conical reflecting surface and said detector, and means for directing radiant energy from said interior conical reflecting surface to said second node location within said main body comprising a second light conducting rod.

6. The probe of claim 5, wherein said second rod diameter is greater than about 0.01 inches and less than about 0.100 inches in diameter.

7. The probe of claim 1, wherein said means for directing radiant energy from said source to said first node location within said main body is a discrete light conducting optical fiber.

8. A probe for optically-based sampling comprising:
a) an elongated main body having a recessed distal end;
b) an elongated extension body adapted for attachment to said main body, having an interior conical reflecting surface facing said main body;
c) a sample chamber disposed between said extension body and said main body in said main body recess, said sample chamber further including an optical entry and an optical exit, and a fluid entry, wherein the sample chamber is adapted to contain a fluid;
d) means for directing radiant energy from an external source to a first node located within said main body;
e) means for communicating radiant energy from said first node to a first portion of said interior conical reflecting surface, comprising a first conducting rod;
f) means for communicating radiant energy from said first portion of said interior conical reflecting surface to a detector; and
g) means for admitting successive samples of such fluid into said sample chamber wherein said means for closing includes a plunger, further including means for adjustably positioning said plunger within said sample chamber.

9. The probe of claim 8, wherein said extension body includes a recessed bore positioned between a first end thereof which joins said main body and said interior conical reflecting surface which is formed in said extension body.

10. The probe of claim 8, wherein said first node comprises transducer means for converting electrical energy in a first medium to optical energy in a second medium.

11. The probe of claim 8, wherein said first light conducting rod is a discrete rod enclosed within a first rod casing.

12. The probe of claim 11, further including a second node location within said main body interposed between a second portion of said interior conical reflecting surface and said detector, and means for directing radiant energy from said interior conical reflecting surface to said second node location within said main body comprising a second light conducting rod.

13. The probe of claim 12, further including means for reflectance detection, comprising an additional light conducting rod displaced from and extending away from an additional surface portion of said interior conical reflecting surface to an additional detector.

14. The probe of claim 13, wherein said additional surface portion is displaced from about 5 azimuth degrees to about 45 azimuth degrees from said first surface portion of said interior conical reflecting surface.

15. The probe of claim 12, wherein said second rod diameter is greater than about 0.01 inches and less than about 0.100 inches in diameter.

16. The probe of claim 8, wherein said means for directing radiant energy from said source to said first node location within said main body is a discrete light conducting optical fiber.

17. A probe for optically-based sampling comprising:
a) an elongated main body having a recessed distal end;
b) an elongated extension body adapted for attachment to said main body, having an interior conical reflecting surface facing said main body;
c) a sample chamber disposed between said extension body and said main body in said main body recess, said sample chamber further including an optical entry and an optical exit, and a fluid entry, wherein the sample chamber is adapted to contain a fluid;
d) means for directing radiant energy from an external source to a first node located within said main body;
e) means for communicating radiant energy from said first node to a first portion of said interior conical reflecting surface, comprising a first conducting rod;
f) means for communicating radiant energy from said first portion of said interior conical reflecting surface to a detector; and
g) means for admitting successive samples of such fluid into said sample chamber wherein said means for admitting includes a plunger, further including electromagnetic means for actuating said plunger.

18. A probe for optically-based sampling comprising:
a) an elongated main body having a recessed distal end;
b) an elongated extension body adapted for attachment to said main body, having an interior conical reflecting surface facing said main body;
c) a sample chamber disposed between said extension body and said main body in said main body recess, said sample chamber further including an optical entry and an optical exit, and a fluid entry, wherein the sample chamber is adapted to contain a fluid;
d) means for directing radiant energy from an external source to a first node located within said main body;
e) means for communicating radiant energy from said first node to a first portion of said interior conical reflecting surface, comprising a first conducting rod;
f) means for communicating radiant energy from said first portion of said interior conical reflecting surface to a detector; and
g) means for admitting successive samples of such fluid into said sample chamber wherein said means for admitting includes a plunger, further including pneumatic means for actuating said plunger.

19. A probe for optically-based sampling comprising:
a) an elongated main body having a recessed distal end;
b) an elongated extension body adapted for attachment to said main body, having an interior conical reflecting surface facing said main body;
c) a sample chamber disposed between said extension body and said main body in said main body recess, said sample chamber further including an optical entry and an optical exit, and a fluid entry, wherein the sample chamber is adapted to contain a fluid;
d) means for directing radiant energy from an external source to a first node located within said main body;
e) means for communicating radiant energy from said first node to a first portion of said interior conical reflecting surface, comprising a first conducting rod;
f) means for communicating radiant energy from said first portion of said interior conical reflecting surface to a detector; and
g) means for admitting successive samples of such fluid into said sample chamber
wherein said means for admitting comprises an interior central chamber in the extension body which chamber includes a necked-down portion of reduced cross section, and said means for admitting comprises means for closing said chamber at said necked-down portion.

20. The probe of claim 19, wherein said extension body includes a recessed bore positioned between a first end thereof which joins said main body and said interior conical reflecting surface which is formed in said extension body.

21. The probe of claim 19, wherein said first node comprises transducer means for converting electrical energy in a first medium to optical energy in a second medium.

22. The probe of claim 19, wherein said first light conducting rod is a discrete rod enclosed within a first rod casing.

23. The probe of claim 22, further including a second node location within said main body interposed between a second portion of said interior conical reflecting surface and said detector, and means for directing radiant energy from said interior conical reflecting surface to said second node location within said main body comprising a second light conducting rod.

24. The probe of claim 23, wherein said second rod diameter is greater than about 0.01 inches and less than about 0.100 inches in diameter.

25. The probe of claim 23, further including means for reflectance detection, comprising an additional light conducting rod displaced from and extending away from an additional surface portion of said interior conical reflecting surface to an additional detector.

26. The probe of claim 19, wherein said means for directing radiant energy from said source to said first node location within said main body is a discrete light conducting optical fiber.

27. A probe for optically-based sampling comprising:
a) an elongated main body having a recessed distal end;
b) an elongated extension body adapted for attachment to said main body, having an interior conical reflecting surface facing said main body;
c) a sample chamber disposed between said extension body and said main body in said main body recess, said sample chamber further including an optical entry and an optical exit, and a fluid entry, wherein the sample chamber is adapted to contain a fluid;
d) means for directing radiant energy from an external source to a first node located within said main body;
e) means for communicating radiant energy from said first node to a first portion of said interior conical reflecting surface, comprising a first conducting rod;
f) means for communicating radiant energy from said first portion of said interior conical reflecting surface to a detector; and
g) means for admitting successive samples of such fluid into said sample chamber;
wherein said means for admitting includes a plunger, further including means for actuating said plunger for closing said means for admitting.

28. The probe of claim 27, wherein said extension body includes a recessed bore positioned between a first end thereof which joins said main body and said interior conical reflecting surface is formed in said extension body.

29. The probe of claim 28, wherein said extension body recessed bore includes an inner wall and a radially inward surface joining said inner wall to said interior conical reflecting surface.

30. The probe of claim 27, further including adhesive means for joining said extension body to said main body.

31. The probe of claim 2, wherein said main body includes a fluid port, further including means for fluid communication between said sample chamber and said fluid port.

32. The probe of claim 27, wherein said first node comprises transducer means for converting electrical energy in a first medium to optical energy in a second medium.

33. The probe of claim 27, wherein said means for directing radiant energy from said source to a first node location within said main body is a discrete light conducting optical fiber.

34. The method of optical sensing characteristics of a fluid in a sample chamber in a probe which comprises:
a) admitting a first one of multiple samples of a fluid through said chamber via an entry and then closing said chamber with a plunger to form a discrete sample;
b) opening said chamber entry to admit a succeeding fluid sample to enter said chamber via said entry;
c) passing an input signal to a first node within said probe, said first node containing an end of a first, discrete light-conducting rod;
d) conducting said input signal from said first node through said first rod as light energy to a first portion of an interior conical reflecting surface;
e) reflecting said input signal from said first portion of said interior conical reflecting surface to a second portion of said interior conical reflecting surface;
f) collecting as an output optical signal at least a portion of the light reflected from said second portion of said interior conical reflecting surface; and
g) directing said output optical signal to a detector within said probe.

35. The method of claim 34, wherein said detector is a first detector, and wherein a reflectance optical signal is carried by an additional light-conducting rod from an additional node located within said probe, further including the step of transferring the reflectance optical signal via an optical fiber pathway to an additional detector.

36. The method of claim 34, wherein a reflectance optical signal is carried by an additional light-conducting rod from an additional node located within said probe, further including the step of converting the reflectance optical signal to an electrical signal in said additional node.

37. The method of claim 34, wherein said detector comprises means for converting an optical signal to an electrical signal, further including the step of converting the output optical signal to an electrical signal.

38. The method of claim 34, wherein said first node comprises means for converting an electrical signal to an optical signal, further including the step of converting an electrical input signal to an optical input signal.

39. The method of claim 34, wherein the output optical signal is carried by a second light-conducting rod to a second node located within said probe, further including the step of transferring the output optical signal via an optical fiber pathway to said detector.

40. The method of claim 34, wherein the output optical signal is carried by a second light-conducting rod to a second node located within said probe, further including the step of converting the output optical signal to an electrical output signal in said second node.

* * * * *